US012697355B2

(12) United States Patent
Itescu

(10) Patent No.: US 12,697,355 B2
(45) Date of Patent: Aug. 4, 2026

(54) METHOD FOR TREATING INFLAMMATORY LUNG DISEASES USING MESENCHYMAL LINEAGE PRECURSOR OR STEM CELLS

(71) Applicant: Mesoblast International Sárl, Meyrin (CH)

(72) Inventor: Silviu Itescu, Melbourne (AU)

(73) Assignee: Mesoblast International Sárl, Meyrin (CH)

( * ) Notice: Subject to any disclaimer, the term of this patent is extended or adjusted under 35 U.S.C. 154(b) by 767 days.

(21) Appl. No.: 17/905,742

(22) PCT Filed: Mar. 4, 2021

(86) PCT No.: PCT/EP2021/055483
§ 371 (c)(1),
(2) Date: Sep. 6, 2022

(87) PCT Pub. No.: WO2021/176001
PCT Pub. Date: Sep. 10, 2021

(65) Prior Publication Data
US 2023/0293589 A1 Sep. 21, 2023

(30) Foreign Application Priority Data

Mar. 5, 2020 (AU) ................................ 2020900685

(51) Int. Cl.
*A61K 35/28* (2015.01)
*A61P 11/00* (2006.01)
(52) U.S. Cl.
CPC .............. *A61K 35/28* (2013.01); *A61P 11/00* (2018.01)
(58) Field of Classification Search
CPC ............ A61P 11/00; A61P 31/14; A61P 31/16
See application file for complete search history.

(56) References Cited

U.S. PATENT DOCUMENTS

| | | | |
|---|---|---|---|
| 5,486,359 A | 1/1996 | Caplan et al. |
| 5,736,396 A | 4/1998 | Bruder et al. |
| 5,827,740 A | 10/1998 | Pittenger |
| 6,030,836 A | 2/2000 | Thiede et al. |
| 6,328,960 B1 | 12/2001 | Mcintosh et al. |
| 6,368,636 B1 | 4/2002 | McIntosh et al. |
| 6,387,369 B1 | 5/2002 | Pittenger et al. |
| 6,685,936 B2 | 2/2004 | Mcintosh et al. |
| 6,797,269 B2 | 9/2004 | Mosca et al. |
| 6,875,430 B2 | 4/2005 | McIntosh et al. |
| 6,936,281 B2 | 8/2005 | Seshi |
| 6,974,571 B2 | 12/2005 | Prockop et al. |
| 7,364,900 B2 | 4/2008 | Black et al. |
| 7,968,088 B2 | 6/2011 | Honmou et al. |
| 8,105,580 B2 | 1/2012 | Fraser et al. |
| 8,142,773 B2 | 3/2012 | Aslan et al. |
| 8,147,824 B2 | 4/2012 | Maziarz et al. |

| | | | |
|---|---|---|---|
| 8,440,177 B2 | 5/2013 | González De La Peña et al. |
| 8,486,695 B2 | 7/2013 | Danilkovitch et al. |
| 8,637,004 B2 | 1/2014 | Danilkovich et al. |
| 9,301,978 B2 | 4/2016 | Itescu et al. |
| 9,694,035 B2 | 7/2017 | Aggarwal et al. |
| 9,828,586 B2 | 11/2017 | Tom et al. |
| 9,888,679 B2 | 2/2018 | Ghosh |
| 9,943,547 B2 | 4/2018 | Aggarwal et al. |
| 9,963,678 B2 | 5/2018 | Tom et al. |
| 10,105,394 B2 | 10/2018 | Itescu et al. |
| 10,206,951 B2 | 2/2019 | Bernard |
| 10,550,369 B2 | 2/2020 | Tom et al. |
| 10,668,101 B2 | 6/2020 | Aggarwal et al. |
| 10,716,814 B2 | 7/2020 | Aggarwal et al. |
| 10,729,727 B2 | 8/2020 | Aggarwal et al. |
| 10,828,334 B1 | 11/2020 | Aggarwal et al. |
| 10,849,932 B2 | 12/2020 | Itescu et al. |
| 10,960,025 B2 | 3/2021 | Aggarwal et al. |
| 11,389,484 B2 | 7/2022 | Aggarwal et al. |
| 11,491,188 B2 | 11/2022 | Itescu et al. |
| 11,685,899 B2 | 6/2023 | Simmons et al. |
| 11,708,560 B2 | 7/2023 | Tom et al. |
| 11,795,435 B2 | 10/2023 | Simmons et al. |
| 11,821,004 B2 | 11/2023 | Danilkovitch et al. |
| 12,115,194 B2 | 10/2024 | Itescu et al. |
| 12,215,352 B2 | 2/2025 | Simmons et al. |

(Continued)

FOREIGN PATENT DOCUMENTS

| | | |
|---|---|---|
| CN | 101626772 A | 1/2010 |
| CN | 105796598 A | 7/2016 |

(Continued)

OTHER PUBLICATIONS

Kebriaei P, Hayes J, Daly A, Uberti J, Skerrett D, Shpall E, Martin PJ. A Phase 3 Randomized Study of Remestemcel-L versus Placebo Added to Second-Line Therapy in Patients with Steroid-Refractory Acute Graft-versus-Host Disease. Biol Blood Marrow Transplant. 2020 (Year: 2020).*
Marquez-Curtis LA, Janowska-Wieczorek A, McGann LE, Elliott JA. Mesenchymal stromal cells derived from various tissues: Biological, clinical and cryopreservation aspects. Cryobiology. Oct. 2015;71(2):181-97. doi: 10.1016/j.cryobiol.2015.07.003. Epub Jul. 14, 2015. PMID: 26186998. (Year: 2015).*
Sun Z, Li F, Zhou X, Chung KF, Wang W, Wang J. Stem cell therapies for chronic obstructive pulmonary disease: current status of pre-clinical studies and clinical trials. J Thorac Dis. Feb. 2018;10(2):1084-1098. doi: 10.21037/jtd.2018.01.46. PMID: 29607186; PMCID: PMC5864644. (Year: 2018).*

(Continued)

*Primary Examiner* — Christopher M Babic
*Assistant Examiner* — Qinhua Gu
(74) *Attorney, Agent, or Firm* — Sterne, Kessler, Goldstein & Fox P.L.L.C.

(57) ABSTRACT

The present disclosure relates to method of treating or preventing an inflammatory lung disease in a subject in need thereof, the method comprising administering to the subject a composition comprising mesenchymal lineage precursor or stem cells (MLPSCs).

15 Claims, 4 Drawing Sheets

(56) References Cited

U.S. PATENT DOCUMENTS

Figure 1:
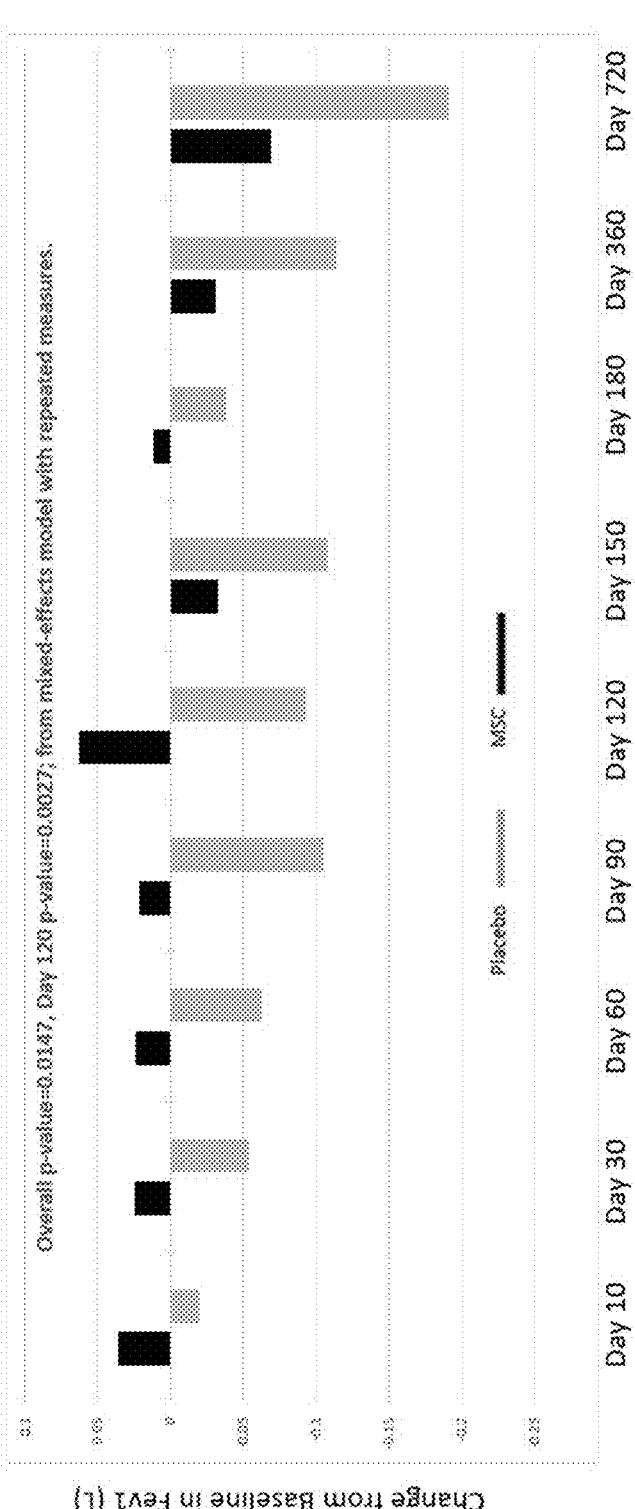

| | | |
|---|---|---|
| 12,410,405 B2 | 9/2025 | Tom et al. |
| 12,473,547 B2 | 11/2025 | Brink et al. |
| 2002/0044923 A1 | 4/2002 | Mosca et al. |
| 2002/0064519 A1 | 5/2002 | Bruder et al. |
| 2003/0118567 A1 | 6/2003 | Stewart |
| 2004/0018174 A1 | 1/2004 | Palasis |
| 2004/0033214 A1 | 2/2004 | Young et al. |
| 2004/0166097 A1 | 8/2004 | Prockop et al. |
| 2005/0239897 A1 | 10/2005 | Pittenger et al. |
| 2006/0083720 A1 | 4/2006 | Fraser et al. |
| 2007/0253931 A1 | 11/2007 | Varney et al. |
| 2007/0258963 A1 | 11/2007 | Danilkovitch et al. |
| 2008/0095749 A1 | 4/2008 | Aggarwal et al. |
| 2008/0132450 A1 | 6/2008 | Lee |
| 2008/0213227 A1 | 9/2008 | Aggarwal et al. |
| 2009/0169522 A1 | 7/2009 | Danilkovitch et al. |
| 2009/0180997 A1 | 7/2009 | Pittenger et al. |
| 2009/0208463 A1 | 8/2009 | Pittenger et al. |
| 2009/0214487 A1 | 8/2009 | Varney et al. |
| 2009/0220464 A1 | 9/2009 | Aggarwal et al. |
| 2009/0324609 A1 | 12/2009 | Lodie et al. |
| 2010/0040583 A1 | 2/2010 | Falanga |
| 2010/0172885 A1 | 7/2010 | Pittenger et al. |
| 2010/0330048 A1 | 12/2010 | Aggarwal et al. |
| 2011/0027238 A1 | 2/2011 | Aggarwal et al. |
| 2011/0142807 A1 | 6/2011 | Pittenger et al. |
| 2011/0189768 A1 | 8/2011 | Danilkovitch et al. |
| 2011/0311496 A1 | 12/2011 | Pittenger et al. |
| 2011/0318314 A1 | 12/2011 | Aggarwal et al. |
| 2011/0318315 A1 | 12/2011 | Aggarwal et al. |
| 2012/0052049 A1 | 3/2012 | Woods et al. |
| 2012/0087933 A1 | 4/2012 | Tom et al. |
| 2012/0201791 A1 | 8/2012 | Yoo |
| 2012/0269774 A1 | 10/2012 | Ichim et al. |
| 2013/0259841 A1 | 10/2013 | Danilkovitch et al. |
| 2014/0105872 A1 | 4/2014 | Danilkovitch et al. |
| 2014/0134140 A1 | 5/2014 | Caplan |
| 2014/0248244 A1 | 9/2014 | Danilkovitch et al. |
| 2014/0328807 A1 | 11/2014 | Aggarwal et al. |
| 2015/0004693 A1 | 1/2015 | Danilkovitch et al. |
| 2015/0272997 A1 | 10/2015 | Aggarwal et al. |
| 2015/0307844 A1 | 10/2015 | Sturm |
| 2016/0199413 A1 | 7/2016 | Simonson et al. |
| 2016/0271180 A1 | 9/2016 | Yamashita |
| 2017/0106023 A1 | 4/2017 | Itescu et al. |
| 2017/0107495 A1 | 4/2017 | Itescu |
| 2017/0340674 A1 | 11/2017 | Itescu et al. |
| 2018/0008642 A1 | 1/2018 | Danilkovitch et al. |
| 2018/0037867 A1 | 2/2018 | Simmons et al. |
| 2018/0087032 A1 | 3/2018 | Danilkovitch et al. |
| 2019/0240259 A1 | 8/2019 | Aggarwal et al. |
| 2020/0197444 A1 | 6/2020 | Danilkovich et al. |
| 2020/0231936 A1 | 7/2020 | Tom et al. |
| 2020/0325450 A1 | 10/2020 | Itescu et al. |
| 2021/0163932 A1 | 6/2021 | Brink et al. |
| 2021/0169940 A1 | 6/2021 | Bernard |
| 2022/0079991 A1 | 3/2022 | Itescu |
| 2022/0143097 A1 | 5/2022 | Itescu et al. |
| 2022/0160776 A1 | 5/2022 | Itescu et al. |
| 2022/0226386 A1 | 7/2022 | Itescu |
| 2022/0275337 A1 | 9/2022 | Devine et al. |
| 2023/0076630 A1 | 3/2023 | Aggarwal et al. |
| 2023/0089901 A1 | 3/2023 | Danilkovich et al. |
| 2023/0097931 A1 | 3/2023 | Itescu |
| 2023/0104108 A1 | 4/2023 | Itescu |
| 2023/0165904 A1 | 6/2023 | Itescu |
| 2023/0172991 A1 | 6/2023 | Itescu |
| 2023/0220349 A1 | 7/2023 | Simmons |
| 2023/0293590 A1 | 9/2023 | Itescu |
| 2023/0346846 A1 | 11/2023 | Itescu et al. |
| 2023/0398154 A1 | 12/2023 | Itescu et al. |
| 2024/0041934 A1 | 2/2024 | Itescu et al. |
| 2024/0091266 A1 | 3/2024 | Itescu et al. |
| 2024/0117315 A1 | 4/2024 | Tom et al. |
| 2024/0197787 A1 | 6/2024 | Itescu et al. |
| 2024/0207323 A1 | 6/2024 | Itescu et al. |
| 2024/0301356 A1 | 9/2024 | Danilkovich et al. |
| 2025/0032552 A1 | 1/2025 | Itescu |
| 2025/0090589 A1 | 3/2025 | Itescu et al. |
| 2025/0129337 A1 | 4/2025 | Simmons et al. |
| 2025/0161365 A1 | 5/2025 | Itescu et al. |
| 2025/0312379 A1 | 10/2025 | Danilkovich et al. |
| 2025/0319428 A1 | 10/2025 | Horst et al. |
| 2026/0035666 A1 | 2/2026 | Tom et al. |
| 2026/0069635 A1 | 3/2026 | Itescu |

FOREIGN PATENT DOCUMENTS

| | | |
|---|---|---|
| CN | 111297899 A | 6/2020 |
| CN | 112522191 A | 3/2021 |
| EP | 2476751 A1 | 7/2012 |
| EP | 3583945 A1 | 12/2019 |
| ES | 2385450 T3 | 7/2012 |
| WO | WO-9951247 A1 | 10/1999 |
| WO | WO-0126470 A1 | 4/2001 |
| WO | WO-2004003164 A2 | 1/2004 |
| WO | WO-2005093044 A1 | 10/2005 |
| WO | WO-2006112365 A1 | 10/2006 |
| WO | WO-2007087139 A2 | 8/2007 |
| WO | WO-2008116157 A2 | 9/2008 |
| WO | WO-2009028870 A2 | 3/2009 |
| WO | WO-2010019886 A1 | 2/2010 |
| WO | WO-2012048093 A2 | 4/2012 |
| WO | WO-2015016761 A2 | 2/2015 |
| WO | WO-2015077624 A1 | 5/2015 |
| WO | WO-2016086020 A1 | 6/2016 |
| WO | WO-2016102601 A1 | 6/2016 |
| WO | WO-2016139340 A1 | 9/2016 |
| WO | WO-2018151046 A1 | 8/2018 |
| WO | WO-2018202853 A1 | 11/2018 |
| WO | WO-2019051623 A1 | 3/2019 |
| WO | WO-2019102268 A1 | 5/2019 |
| WO | WO-2020141473 A1 | 7/2020 |
| WO | WO-2020141483 A1 | 7/2020 |
| WO | WO-2020157660 A1 | 8/2020 |
| WO | WO-2020234450 A1 | 11/2020 |
| WO | WO-2021007180 A1 | 1/2021 |
| WO | WO-2021024207 A1 | 2/2021 |
| WO | WO-2021165420 A1 | 8/2021 |
| WO | WO-2021176001 A1 | 9/2021 |
| WO | WO-2021180850 A1 | 9/2021 |
| WO | WO-2021180851 A1 | 9/2021 |
| WO | WO-2021198454 A1 | 10/2021 |
| WO | WO-2021222389 A1 | 11/2021 |
| WO | WO-2022034467 A1 | 2/2022 |
| WO | WO-2022034506 A1 | 2/2022 |
| WO | WO-2022132986 A1 | 6/2022 |
| WO | WO-2022159731 A1 | 7/2022 |
| WO | WO-2023238074 A1 | 12/2023 |

OTHER PUBLICATIONS

Zhao R, Su Z, Wu J, Ji HL. Serious adverse events of cell therapy for respiratory diseases: a systematic review and meta-analysis. Oncotarget. May 2, 2017;8(18):30511-30523. doi: 10.18632/oncotarget. 15426. PMID: 28430622; PMCID: PMC5444761. (Year: 2017).*

Weiss DJ, Casaburi R, Flannery R, LeRoux-Williams M, Tashkin DP. A placebo-controlled, randomized trial of mesenchymal stem cells in COPD. Chest. Jun. 2013;143(6):1590-1598. doi: 10.1378/ chest.12-2094. PMID: 23172272; PMCID: PMC4694112. (Year: 2013).*

Weiss, D.J., et al., "A Placebo-controlled, randomized trial of mesenchymal stem cells in COPD," Chest 143(6):1590-1598, Elsevier, Netherlands (Jun. 2013).

Simonson, O.E., et al., "In vivo effects of mesenchymal stromal cells in two patients with severe acute respiratory distress syndrome," Stem Cells Transl Med 4(10):1199-213, Wiley, United States (Aug. 2015).

Matthay, M.A., et al., "Treatment with allogeneic mesenchymal stromal cells for moderate to severe acute respiratory distress syndrome (START study): a randomised phase 2a safety trial," Lancet Respir Med 7(2):154-162, Elsevier, Netherlands (Nov. 2018).

(56)　　　　References Cited

OTHER PUBLICATIONS

Liu, Y., et al., "Clinical features and progression of acute respiratory distress syndrome in coronavirus disease 2019" medRxiv, Cold Spring Harbor Laboratory, United States (Feb. 2020).

Leng, Z., et al., "Transplantation of ACE2-Mesenchymal Stem Cells Improves the Outcome of Patients with COVID-19 Pneumonia," Aging and Disease 11(2):216-228, JKL International on behalf of the International Society on Aging and Disease, United States (Apr. 2020).

Balnis, J., et al., "Unique Inflammatory Profile is Associated With Higher SARS-CoV-2 Acute Respiratory Distress Syndrome (ARDS) Mortality," 17 pages, (Aug. 2020).

Bode, S., et al., "Recent Advances in the Diagnosis and Treatment of Hemophagocytic Lymphohistiocytosis," Arthritis Research & Therapy 14(3):213, 1-12, BioMed Central, United Kingdom (Jun. 2012).

Callahan, V., et al., "The Pro-inflammatory Chemokines CXCL9, CXCL 10 and CXCL11 Are Upregulated Following SARS-CoV-2 Infection in an AKT-dependent Manner," Viruses 13(6):1062, 1-18, MDPI, Switzerland (Jun. 2021).

Chen, X., et al., "The Interaction Between Mesenchymal Stem Cells and Steroids During Inflammation," Cell Death & Disease 5(1):e1009, 1-12, Nature Pub. Group, United Kingdom (Jan. 2014).

Chua, R.L., "COVID-19 severity correlates with airway epithelium-immune cell interactions identified by single-cell analysis," Nature Biotechnology 38(8):970-979, Nature America Publishing, United States (Aug. 2020).

Crayne, C.B., et al., "The Immunology of Macrophage Activation Syndrome," Frontiers in Immunology 10:119, 1-11, Frontiers Research Foundation, Switzerland (Feb. 2019).

Humblet-Baron, S., et al., "IFN-γ and CD25 Drive Distinct Pathologic Features During Hemophagocytic Lymphohistiocytosis," The Journal of Allergy and Clinical Immunology 143(6):2215-2226.e7, Mosby, United States (2018).

Kaneko, N., et al., "Expansion of Cytotoxic CD4+ T Cells in the Lungs in Severe Covid-19," medRxiv 2021.03.23.21253885, 1-46, Cold Spring Harbor Laboratory, United States (Mar. 2021).

Mathew, D., et al., "Deep Immune Profiling of Covid-19 Patients Reveals Distinct Immunotypes With Therapeutic Implications," Science 369(6508):eabc8511, 1-18, American Association for the Advancement of Science, United States (Sep. 2020).

Meckiff, B.J., et al., "Single-cell Transcriptomic Analysis of SARS-CoV-2 Reactive CD4+ T Cells," bioRxiv 2020.06.12.148916, 1-37, Cold Spring Harbor Laboratory, United States (Jun. 2020).

Mehta, P., "COVID-19: Consider Cytokine Storm Syndromes and Immunosuppression," Lancet 395(10229):1033-1034, Elsevier, United kingdom (Mar. 2020).

Meizlish, M.L., "A Neutrophil Activation Signature Predicts Critical Illness and Mortality in COVID-19," Blood Advances 5(5):1164-1177, American Society of Hematology, United States (Mar. 2021).

Moderbacher, C.R., et al., "Antigen-Specific Adaptive Immunity to SARS-CoV-2 in Acute COVID-19 and Associations with Age and Disease Severity," Cell 183(4):996-1012.e19, Cell Press, United States (Nov. 2020).

Seguin, A., et al., "Pulmonary Involvement in Patients With Hemophagocytic Lymphohistiocytosis," Chest 149(5):1294-1301, Elsevier, United States (May 2016).

Sette, A and Crotty, S., "Adaptive Immunity to SARS-CoV-2 and COVID-19," Cell 184(4):861-880, Cell Press, United States (Feb. 2021).

Stehlik, P., "Repeat Testing for SARS-CoV-2: Persistence of Viral RNA is Common, and Clearance is Slower in Older People," The Medical Journal of Australia 214(10):468-470, Australian Medical Publishing Co., Australia (Jun. 2021).

Yan, Y., et al., "CCL19 and CCR7 Expression, Signaling Pathways, and Adjuvant Functions in Viral Infection and Prevention," Frontiers in Cell and Developmental Biology 7:212, 1-13, Frontiers Media S.A., Switzerland (Oct. 2019).

Zhou, B., "Utility of Ferritin, Procalcitonin, and C-reactive Protein in Severe Patients with 2019 Novel Coronavirus Disease," Research Square, 1-12, Springer Nature, Germany (Mar. 2020).

Zhou, Y., et al., "Pathogenic T-cells and Inflammatory Monocytes Incite Inflammatory Storms in Severe COVID-19 Patients," National Science Review 7(6):998-1002, Oxford University Press, United Kingdom (Jun. 2020).

Zhu, L., et al., "Cellular Metabolism and Macrophage Functional Polarization," International Reviews of Immunology 34(1):82-100, Informa Healthcare, United Kingdom (Jan. 2015).

Afzali, B., et al., "The Role of T helper 17 (Th17) and regulatory T cells (Treg) in human organ transplantation and autoimmune disease," Clinical and Experimental Immunology 148(1):32-46, Blackwell Scientific Publications, England (Apr. 2007).

Aggarwal, S. and Pittenger, M.F., "Human Mesenchymal Stem Cells Modulate Allogeneic Immune Cell Responses," Blood 105(4):1815-1822, American Society of Hematology, United States (Feb. 2005).

American Association for Respiratory Care: AARC Clinical Practice Guideline: Spirometry, Respiratory Care 41:629-638 (1996 Update).

Anonymous: "Athersys Provides Update on One-Year ARDS Study Data," News Release 1-5 pages (Jan. 2020).

Anonymous: "Mesoblast to evaluate anti-inflammatory cell therapy remestemcel-L for treatment of Covid-19 lung disease," 3 pages (2020).

Atluri, S., et al., "Expanded Umbilical Cord Mesenchymal Stem Cells (UC-MSCs) as a Therapeutic Strategy in Managing Critically Ill COVID-19 Patients: The Case for Compassionate Use," Pain Physician 23(2):E71-E83 American Society of Interventional Pain Physicians, United States (Mar. 2020).

ATS Committee on Proficiency Standards for Clinical Pulmonary Function Laboratories., "ATS Statement: Guidelines for the Six-minute Walk Test," American Journal of Respiratory and Critical Care Medicine 166(1):111-117, American Thoracic Society, United States (Jul. 2002).

Barry, F.P and Murphy, J.M., "Mesenchymal Stem Cells: Clinical Application and Biological Characterization," International Journal of Biochemistry & Cell Biology 36:568-584, Elsevier, Netherlands (Apr. 2004).

Barry, F.P., et al., "Biology And Clinical Applications of Mesenchymal Stem Cells, " Birth Defects Research Part C: Embryo Today 69(3):250-256, Wiley Periodicals, Inc., United States (Aug. 2003).

Bartholomew, A., et al., "Mesenchymal Stem Cells Suppress Lymphocyte Proliferation In Vitro And Prolong Skin Graft Survival In Vivo," Experimental Hematology 30(1):42-48, Elsevier Science Inc., Netherlands (Jan. 2002).

Bobis, S., et al., "Mesenchymal Stem Cells: Characteristics and Clinical Applications," Folia Histochemica ET Cytobiologica 44(4):215-230, Polish Histochemical and Cytochemical Society at VM Media, Poland (2006).

Borzone, G., et al., "Bleomycin-induced Chronic Lung Damage Does Not Resemble Human Idiopathic Pulmonary Fibrosis," American Journal of Respiratory and Critical Care Medicine 163(7):1648-1653, American Thoracic Society, United States (Jun. 2001).

Boston Scientific Corporation, "Boston Scientific and Osiris Therapeutics Announce Stem Cell Alliance," accessed at URL:[www.ptca.org/press_rel/20030311pr_boston.html] on Apr. 12, 2023, 2 pages (Mar. 11, 2003).

Boucher, R.C, "New Concepts of the Pathogenesis of Cystic Fibrosis Lung Disease," The European Respiratory Journal 23(1):146-158, European Respiratory Society, England (Jan. 2004).

Bowden, D.H, "Unraveling Pulmonary Fibrosis: the Bleomycin Model," Laboratory Investigation 50(5):487-488, Nature Publishing Group, United States (May 1984).

Brass, D.M., et al., "Reduced Tumor Necrosis Factor-α and transforming Growth Factor-β1 Expression in the Lungs of Inbred Mice that Fail to Develop Fibroproliferative Lesions Consequent to Asbestos Exposure," American Journal of Pathology 154(3):853-862, Elsevier, United States (Mar. 1999).

Burand, A.J., et al., "Function of Cryopreserved MSCs with and without IFN-γ pre-licensing is Context Dependent," Stem Cells 35(5):1437-1439, Wiley, United States (Nov. 2016).

(56) References Cited

OTHER PUBLICATIONS

Chen, J., et al., "Clinical Study of Mesenchymal Stem Cell Treatment for Acute Respiratory Distress Syndrome Induced by Epidemic Influenza A (H7N9) Infection: A Hint for COVID-19 Treatment," Engineering 6(10):1153-1161, Higher Education Press, China (Oct. 2020).

Collier, M., et al., "Understanding Wound Inflammation," Nursing Times 99(25:63-64, Macmillian Journals, England (Jun. 2003).

Conese, M., et al., "Stem Cells and Cystic Fibrosis," Cystic Fibrosis 5(3):141-143, Elsevier, Netherlands (Aug. 2006).

Czitrom, A.A., "The Immune Response: The Afferent Arm," Clinical Orthopaedics and Related Research (326):11-24, Wolters Kluwer, United States (May 1996).

De Miguel, M.P., et al., "Immunosuppressive Properties of Mesenchymal Stem Cells: Advances and Applications," Current Molecular Medicine 12(5):574-591, Bentham Science Publishers, Netherlands (Jun. 2012).

Deans, R.J and Moseley, A.B, "Mesenchymal Stem Cells: Biology and Potential Clinical Uses," Experimental Hematology 28(8):875-884, Elsevier Science Inc, Netherlands (Aug. 2000).

Devine, S.M., et al., "Mesenchymal Stem Cells Distribute To a Wide Range of Tissues Following Systemic Infusion into Nonhuman Primates," Blood 101(8):2999-3001, American Society of Hematology, United States (Apr. 2003).

Di Nicola, M., et al., "Human Bone Marrow Stromal Cells Suppress T-Lymphocyte Proliferation Induced By Cellular or Nonspecific Mitogenic Stimuli," Blood 99(10):3838-3843, American Society of Hematology, United States (May 2002).

Chang, Y.S., et al., "Human umbilical cord blood-derived mesenchymal stem cells attenuate hyperoxia-induced lung injury in neonatal rats," Cell Transplant 18(8):869-86, Sage Journals, United States (Apr. 2009).

Fischer, U, M., et al., "Pulmonary Passage is a Major Obstacle for Intravenous Stem Cell Delivery: the Pulmonary First-pass Effect," Stem cells and development 18(5):683-692, Mary Ann Liebert, Inc., United States (Jun. 2009).

Gao, J., et al., "The Dynamic in Vivo Distribution of Bone Marrow-derived Mesenchymal Stem Cells After Infusion," Cells, Tissues, Organs 169(1):12-20, Karger, Switzerland (Apr. 2001).

Griffin, M. D., et al.,. "Anti-donor Immune Responses Elicited by Allogeneic Mesenchymal Stem Cells: What Have We Learned so Far?," Immunology and Cell Biology 91(1):40-51, Wiley, United States (Jan. 2013).

Gronthos, S., et al., "Molecular and Cellular Characterisation of Highly Purified Stromal Stem Cells Derived From Human Bone Marrow," Journal of Cell Science 116(Pt 9):1827-1835, Company of Biologists, United Kingdom (May 2003).

Guo, Z., et al., "Biological Features of Mesenchymal Stem Cells From Human Bone Marrow," Chinese Medical Journal 114(9):950-953, Wolters Kluwer-Medknow, China (Sep. 2001).

Hackney, J.A., et al., "A Molecular Profile of a Hematopoietic Stem Cell Niche," PNAS, 99(20): 13061-13066, National Academy of Science, United States (Oct. 2002).

Horwitz, E.M., et al., "Clarification of the Nomenclature for MSC: The International Society for Cellular Therapy Position Statement," Cytotherapy 7(5):393-395, Elsevier, United Kingdom (Jan. 2005).

International Search Report and Written Opinion for International Application No. PCT/EP2021/055483, European Patent Office, Netherlands, mailed on Jun. 8, 2021,14 pages.

Izadpanah, R., et al., "Biologic Properties of Mesenchymal Stem Cells Derived From Bone Marrow and Adipose Tissue," Journal of Cellular Biochemistry 99(5):1285-1297, Wiley-Liss, United States (Dec. 2006).

Jiang, Y., et al., "Pluripotency of Mesenchymal Stem Cells Derived From Adult Marrow," Nature, 418(6893):41-49, Nature Publishing Group, United Kingdom (Jul. 2002).

Kassem, M., "Mesenchymal Stem Cells: Biological Characteristics and Potential Clinical Applications," Cloning and Stem Cells 6(4):369-374, Mary Ann Liebert, Inc., United States (Dec. 2004).

Katzenstein, A-L, A., et al., "Idiopathic Pulmonary Fibrosis; Clinical Relevance of Pathologic Classification," Am J Respir Crit Care Med 157(4 Pt 1):1301-1315, American Thoracic Society, United States (Apr. 1998).

Kavanagh, H. and Mahon, B.P., "Allogeneic Mesenchymal Stem Cells Prevent Allergic Airway Inflammation by Inducing Murine Regulatory T Cells," Allergy 66: 523-531, John Wilet & Sons A/S, United States (2011).

Kotton, D.N., et al., "Bone Marrow-derived Cells as Progenitors of Lung Alveolar Epithelium," Development 128(24):5181-5188, Company of Biologists Limited, England (2001).

Krause, D.S., et al., "Multi-organ, Multi-lineage Engraftment by a Single Bone Marrow-derived Stem Cell," Cell 105(3):369-377, Cell Press, United States (May 2001).

Krebsbach, P.H., et al., "Bone Marrow Stromal Cells: Characterization and Clinical Application," Critical Reviews in Oral Biology and Medicine 10(2):165-181, International Association for Dental Research, United States (1999).

Le Blanc, K. and Ringden, O., "Immunobiology of Human Mesenchymal Stem Cells and Future Use in Hematopoietic Stem Cell Transplantation," Biology of Blood and Marrow Transplantation 11(5):321-334, Carden Jennings Publishing, United States (May 2005).

Le Blanc, K., "Immunomodulatory Effects of Fetal and Adult Mesenchymal Stem Cells," Cytotherapy 5(6):485-489, Elsevier, United Kingdom (2003).

Le Blanc, K., et al., "HLA Expression and Immunologic Properties of Differentiated and Undifferentiated Mesenchymal Stem Cells," Experimental Hematology 31(10):890-896, Elsevier Science Inc, Netherlands (Oct. 2003).

Lindner, U., et al., "Mesenchymal Stem or Stromal Cells: Toward a Better Understanding of Their Biology?," Transfusion Medicine and Hemotherapy 37(2):75-83, S. Karger, Switzerland (Apr. 2010).

Lucchini, G., et al., "Platelet-lysate-expanded Mesenchymal Stromal Cells as a Salvage Therapy for Severe Resistant Graft-versus-host Disease in a Pediatric Population," Biology of blood and marrow transplantation 16(9):1293-1301, Carden Jennings Publishing, United States (Sep. 2010).

Lukomska, B., et al., "Challenges and Controversies in Human Mesenchymal Stem Cell Therapy," Stem cells international 2019: Article ID (9628536), SAGE-Hindawi Access to Research, United States (Apr. 2019).

Mackenzie, T.C. and Flake, A.W., "Human Mesenchymal Stem Cells Persist, Demonstrate Site-specific Multipotential Differentiation, and Are Present in Sites of Wound Healing and Tissue Regeneration After Transplantation Into Fetal Sheep," Blood Cells, Molecules & Diseases 27(3):601-604, Academic Press, United States (May 2001).

Maitra, B., et al., "Human Mesenchymal Stem Cells Support Unrelated Donor Hematopoietic Stem Cells and Suppress T-cell Activation," Bone Marrow Transplant 33(6):597-604, Nature Publishing Group, United Kingdom (Mar. 2004).

Martire, A., et al., "Mesenchymal stem cells attenuate inflammatory processes in the heart and lung via inhibition of TNF signaling," Basic Res Cardiol 111(5):54, Springer Berlin Heidelberg, Germany (Sep. 2016).

Mcintosh, K. and Bartholomew, A., "Stromal Cell Modulation of The Immune System," Graft Review 3(6):324-328, SAGE Publications, United States (2000).

Mcnulty, K and Janes, S.M., "Stem Cells and Pulmonary Fibrosis: Cause or Cure?," Proc Am Thorac Soc 9(3):164-171, American Thoracic Society, United States (Jul. 2012).

Meisel, R., et al., "Human bone marrow stromal cells inhibit allogenic T-cell responses by indoleamine 2,3-dioxygenase-mediated tryptophan degradation," Immunobiology 103(12):4619-4621, The American Society of Hematology, United States (2004).

Melgar, S., et al., "Over-expression of Interleukin 10 in Mucosal T Cells of Patients With Active Ulcerative Colitis," Clinical and Experimental Immunology 134(1):127-137, Blackwell Scientific Publications, United Kingdom (Oct. 2003).

Mesoblast Limited, "Mesoblast Heart Failure Cell Therapy Receives Orphan Drug Designation From FDA For Prevention Of Gastrointestinal Bleeding In Patients With Left Ventricular Assist Devices,"

(56)        References Cited

OTHER PUBLICATIONS investorsmedia.mesoblast.com, accessed at URL: [ http://investorsmedia. mesoblast.com/static-files/c08cebeb-456b-49d4-8e0d-cfc5dfllOd9e] on Mar. 31, 2020, 3 pages (Jun. 2019).

Neuringer I.P., et al., "Stem Cells and Repair of Lung Injuries," Respiratory Research, 5, 6, (Jul. 2004).

Newman, R.E., et al., "Treatment of Inflammatory Diseases With Mesenchymal Stem Cells," Inflammation & Allergy Drug Targets 8(2):110-123, Bentham Science Publishers, United Arab Emirates (Jun. 2009).

Niederwieser, D., et al., "Hematopoietic stem cell transplantation activity worldwide in 2012 and a SWOT analysis of the Worldwide Network for Blood and Marrow Transplantation Group including the global survey," Bone marrow transplantation 51(6):778-85, Nature Publishing Group, United Kingdom (Jun. 2016).

Ortiz, L.A., et al., "Mesenchymal Stem Cell Engraftment in Lung Is Enhanced in Response to Bleomycin Exposure and Ameliorates Its Fibrotic Effects," Proceedings of the National Academy of Sciences of the United States of America 100(14):8407-8411, National Academy of Sciences, United States (Jul. 2003).

Pereira, R.F., et al., "Cultured adherent cells from marrow can serve as long-lasting precursor cells for bone, cartilage, and lung in irradiated mice," Proceedings of the National Academy of Sciences of the United States of America 92(11):4587-4861, United States National Academy of Sciences, United States (May 1995).

Pittenger, M. F., for Osiris Therapeutics, "Leaders in Stem Cell Medicine, Applications of Mesenchymal Stem Cells," Press Release, 2 pages (2001).

Pittenger, M.F., et al., "Multilineage Potential of Adult Human Mesenchymal Stem Cells," Science 284(5411):143-147, American Association for the Advancement of Science, United States (Apr. 1999).

Prockop, D.J., "Marrow Stromal Cells as Stem Cells for Nonhematopoietic Tissues," Science 276(5309):71-74, American Association for the Advancement of Science, United States (Apr. 1997).

Rabe, K.F., et al., "Global Strategy for the Diagnosis, Management, and Prevention of Chronic Obstructive Pulmonary Disease: Gold Executive Summary," American Journal of Respiratory and Critical Care Medicine, 176(6):532-555, American Thoracic Society, United States (Sep. 2007).

Ramasamy, R., et al., "The Immunosuppressive Effects of Human Bone Marrow-derived Mesenchymal Stem Cells Target T Cell Proliferation but Not Its Effector Function," Cellular Immunology 251(2):131-136, Elsevier, Netherlands (Feb. 2008).

Rasmusson, I., "Immune Modulation by mesenchymal stem cells," Experimental Cell Research 312:2169-2179, Elsevier, Netherlands (Jul. 2006).

Rayment, E.A., et al., "Concise Review: Mind the Gap: Challenges in Characterizing and Quantifying Cell- and Tissue-based Therapies for Clinical Translation," Stem Cells (Dayton, Ohio) 28(5):996-1004, Oxford University Press, United Kingdom (May 2010).

Rojas, M., et al., "Bone Marrow-derived Mesenchymal Stem Cells in Repair of the Injured Lung," American Journal of Respiratory Cell and Molecular Biology 33(2):145-152, American Thoracic Society, United States (Aug. 2005).

Serhan, C.N., et al.,, "Resolution of Inflammation: State of the Art, Definitions and Terms," The FASEB Journal 21(2):325-332, The Federation, United States (Feb. 2007).

Sherer, Y and Shoenfeld, Y., "Autoimmune Diseases and Autoimmunity Post-bone Marrow Transplantation," Bone Marrow Transplantation 22:873-881, Stockton Press, United Kingdom (Nov. 1998).

Snowden, J.A., et al., "Long-term Outcome of Autoimmune Disease Following Allogeneic Bone Marrow Transplantation," Arthritis and Rheumatism 41(3):453-459, Wiley-Blackwell, United States (Mar. 1998).

Thannickal, V.J., et al., "Mechanisms of Pulmonary Fibrosis," Annual Review of Medicine 55:395-417, Annual Reviews, United States (2004).

Tolar, J., et al., "Concise Review: Hitting the Right Spot With Mesenchymal Stromal Cells," Stem Cells (Dayton, Ohio) 28(8):1446-1555, Oxford University Press, United Kingdom (Aug. 2010).

Tse, W.T., et al., "Suppression of Allogeneic T-cell Proliferation by Human Marrow Stromal Cells: Implications in Transplantation," Transplantation 75(3):389-397, Lippincott Williams & Wilkins, United States (Feb. 2003).

Tuli, R., et al., "Characterization of Multipotential Mesenchymal Progenitor Cells Derived from Human Trabecular Bone," Stem Cells 21(6):681-693, Oxford University Press, United Kingdom (Nov. 2003).

Ullah, I., et al., "Human Mesenchymal Stem Cells-Current Trends and Future Prospective," Bioscience Reports 35(2):e00191, Springer, United States (Apr. 2015).

Van Laar, J.M., et al., "Adult Stem Cells In the Treatment of Autoimmune Diseases," Rheumatology (Oxford) 45(10):1187-1193, Oxford University Press, United Kingdom (Oct. 2006).

Vodyanik, M. A., et al., "A mesoderm-derived precursor for mesenchymal stem and endothelial cells," Cell Stem Cell 7(6):718-729, Cell Press, United States (Dec. 2010).

Wagers, A.J., et al., "Cell Fate Determination From Stem Cells," Gene Therapy 9(10):606-612, Nature Publishing Group, United Kingdom (May 2002).

Wang, G., et al., "Adult Stem Cells From Bone Marrow Stroma Differentiate Into Airway Epithelial Cells: Potential Therapy for Cystic Fibrosis," Proceedings of the National Academy of Sciences of the United States of America 102(1):186-191, National Academy of Sciences, United States (Jan. 2005).

Wang, L., et al., "Efficacy and Safety of Mesenchymal Stromal Cells for the Prophylaxis of Chronic Graft-versus-host Disease After Allogeneic Hematopoietic Stem Cell Transplantation: A Meta-analysis of Randomized Controlled Trials," Annals of Hematology 97(10):1941-1950, Springer Verlag, Germany (Oct. 2018).

Wang, L.-T., et al., "Human mesenchymal stem cells (MSCs) for treatment towards immune- and inflammation-mediated diseases: review of current clinical trials," Journal of Biomedical Science 23:76, BioMed Central, United Kingdom (2016).

Yan, L., et al., "Critical Role of Tumor Necrosis Factor Signaling in Mesenchymal Stem cell-based therapy for autoimmune and inflammatory diseases," Front Immunol 9:1658, Frontiers Media, Switzerland (Jul. 2018).

Zheng, G., et al., "Treatment of Acute Respiratory Distress Syndrome With Allogeneic Adipose-derived Mesenchymal Stem Cells: A Randomized, Placebo-controlled Pilot Study," Respiratory Research 15(1):39, BioMed Central Ltd., United KingdomEngland (Apr. 2014).

Zhou, S. Z., et al., "Adeno-associated Virus 2-Mediated High Efficiency Gene Transfer into Immature and Mature Subsets of Hematopoietic Progenitor Cells in Human Umbilical Cord Blood," The Journal of Experimental Medicine 179(6):1867-1875, Rockefeller University Press, United States (Jun. 1994).

Zinöcker, S. and Vaage J.T., "Rat Mesenchymal Stromal Cells Inhibit T Cell Proliferation but Not Cytokine Production Through Inducible Nitric Oxide Synthase," Frontiers in Immunology 3:62, Frontiers Research Foundation, Switzerland (Apr. 2012).

Ziobro, R., et al., "Ceramide Mediates Lung Fibrosis in Cystic Fibrosis," Biochemical and Biophysical Research Communications 434(4):705-709, Elsevier, United States (May 2013).

Kebriaei, P., et al., "Adult Human Mesenchymal Stem Cells Added to Corticosteroid Therapy for the Treatment of Acute Graft-versus-Host Disease," Biol Blood Marrow Transplant 15:804-811, Elsevier, Netherlands (2009).

He, X., et al., "Umbilical cord-derived mesenchymal stem (stromal) cells for treatment of severe sepsis: a phase 1 clinical trial," Transl Res 199:52-61, Elsevier, Netherlands (Apr. 2018).

Pereira, T., et al., "MSCs Conditioned Media and Umbilical Cord Blood Plasma Metabolomics and Composition," PLOS One 9(11):e113769, Public Library of Science, United States (Nov. 2019).

Prasad, A., et al., "Cytokine Detection In Culture Media Containing 10% FBS—A Comparison Of Two Commonly Used Homogeneous High Throughput Assay Technologies," accessed at https://resources.

(56) References Cited

OTHER PUBLICATIONS perkinelmer.com/corporate/content/featured/sbs2009/pdfs/p7012%
20-%20anu-alphalisa%20vs%20cisbio_15apr09.pdf Perkin Elmer,
Inc., United States (Jan. 2009).

Anonymous, "Newborn Calf Serum S11250: R&D Systems," accessed
at https://www.rndsystems.com/products/newborn-calf-serum_
s11250, 4 pages (Aug. 2010).

Liu, S., et al., "Mesenchymal stem cells as a potential therapy for
COVID-19," Stem Cell Research & Therapy 11:169, Springer
Nature, Germany (May 2020).

Wilson, J.G., et al., "Mesenchymal stem (stromal) cells for treat-
ment of ARDS: a phase 1 clinical trial," Lancet Respir Med
3(1):24-32, Elsevier, Netherlands (Jan. 2015).

Al-Khawaga, S., et al., "Potential application of mesenchymal stem
cells and their exosomes in lung injury: an emerging therapeutic
option for COVID-19 patients," Stem Cell Research & Therapy
11:437, Springer Nature, Germany (Oct. 2020).

Roudsari, P.P., et al., "Auxiliary role of mesenchymal stem cells as
regenerative medicine soldiers to attenuate inflammatory processes
of severe acute respiratory infections caused by COVID-19," Cell
Tissue Bank 21(3):405-425, Springer, Germany (Sep. 2020).

Co-pending Application, U.S. Appl. No. 18/711,167, inventor Itescu,
S., filed May 17, 2024 (Not yet Published).

Co-pending Application, U.S. Appl. No. 18/723,204, inventor Itescu,
S., filed Dec. 23, 2022 (Not yet Published).

Co-pending Application, U.S. Appl. No. 19/086,003, inventor
Danilkovich, A., et al., filed Mar. 20, 2025 (Not yet Published).

Co-pending Application, U.S. Appl. No. 19/137,213, inventor Itescu,
S., et al., filed Jun. 9, 2025 (Not yet Published).

Co-pending Application, U.S. Appl. No. 19/137,193, inventor Itescu,
S., et al., filed Jun. 9, 2025 (Not yet Published).

Co-pending Application, U.S. Appl. No. 19/136,677, inventor Itescu,
S., et al., filed Jun. 6, 2025 (Not yet Published).

Co-pending Application, U.S. Appl. No. 19/136,773, inventor Itescu,
S., et al., filed Jun. 6, 2025 (Not yet Published).

Co-pending Application, U.S. Appl. No. 18/869,064, inventor Horst,
J., et al., filed Nov. 25, 2025 (Not yet Published).

Co-pending Application, U.S. Appl. No. 18/872,445, inventor Itescu,
S., filed Jun. 8, 2023 (Not yet Published).

Co-pending Application, U.S. Appl. No. 18/880,992, inventor Itescu,
S., et al., filed Jan. 3, 2025 (Not yet Published).

Bich, P.L.T., et al., "Allogeneic umbilical cord-derived mesenchymal
stem cell transplantation for treating chronic obstructive pulmonary
disease: a pilot clinical study." Stem cell research & therapy
11(1):60, 1-14, BioMed Central (Springer Nature), United Kingdom
(Feb. 2020).

Cavalli, G., et al., "Interleukin-1 and interleukin-6 inhibition com-
pared with standard management in patients with COVID-19 and
hyperinflammation: a cohort study." The Lancet Rheumatology
3(4): e253-e261, Elsevier Ltd, United Kingdom (Apr. 2021).

Chen, M., et al., "C-reactive protein mediates the association
between leisure-time physical activity and lung function in middle-
aged and older adults." BMC Public Health 20:6, 1-8, BioMed
Central (Springer Nature), United Kingdom (Jan. 2020).

Igarashi, T., et al., "Adiponectin and inflammation markers in
patients with pneumoconiosis." Japanese Journal of Occupational
and Environmental Medicine (JJOMT) 62:184-188, Japanese Soci-
ety of Occupational Medicine and Traumatology, Japan (2014).

Kebriaei, P., et al., "A Phase 3 randomized study of remestemcel-L
versus placebo added to second-line therapy in patients with steroid-
refractory acute graft-versus-host disease." Biology of Blood and
Marrow Transplantation 26:835-844, Elsevier, United States (2019).

Landry, A., et al., "Causes and outcomes of markedly elevated
C-reactive protein levels." Canadian Family Physician 63:e316-
e323, College of Family Physicians of Canada, Canada (Jun. 2017).

Le, P.T.B., et al., "Umbilical cord derived stem cell (Modulatist™)
transplantation for severe chronic obstructive pulmonary disease: a
report of two cases." Biomedical Research and Therapy 3(10):902-
909, BioMedPress, Vietnam (Oct. 2016).

Marquez-Curtis, L.A., et al., "Mesenchymal stromal cells derived
from various tissues: Biological, clinical and cryopreservation aspects."
Cryobiology 71:181-197, Elsevier, United States (Jul. 2015).

Singh, B., et al., "C-Reactive Protein: Clinical Relevance and
Interpretation." StatPearls [Retrieved from the Internet], https://
www.ncbi.nlm.nih. gov/books/NBK441843/, United States (May
2025).

Co-pending Application, U.S. Appl. No. 19/388,629, inventors
Danilkovich, A., et al., filed Nov. 13, 2025 (Not yet Published).

Co-pending Application, U.S. Appl. No. 19/521,804, inventor Itescu,
S., et al., filed Mar. 20, 2026 (Not yet Published).

* cited by examiner

METHOD FOR TREATING INFLAMMATORY LUNG DISEASES USING MESENCHYMAL LINEAGE PRECURSOR OR STEM CELLS

CROSS-REFERENCE TO RELATED APPLICATIONS

The present application is a U.S. national stage entry of International Application No. PCT/EP2021/055483, filed on Mar. 4, 2021, which claims priority to AU Application No. 2020900685, filed on Mar. 5, 2020, each of which is hereby incorporated by reference in its entirety.

FIELD OF THE DISCLOSURE

The present disclosure relates to methods for treating or preventing an inflammatory lung disease in a subject in need thereof.

BACKGROUND

Respiratory ailments, associated with a variety of conditions, are extremely common in the general population. In many cases they are accompanied by inflammation, which aggravates the condition of the lungs. Diseases such as asthma, allergic rhinitis, Chronic Obstructive Pulmonary Disease (COPD), and Acute Respiratory Distress Syndrome (ARDS), among others, are common diseases in industrialized countries, and they account for extremely high health care costs. These diseases have recently been increasing at an alarming rate, both in terms of prevalence, morbidity and mortality. In spite of this, their underlying causes still remain poorly understood.

Accordingly, there remains an unmet therapeutic need in patients with inflammatory lung diseases and/or its associated conditions or symptoms with new treatment options being required.

SUMMARY OF THE DISCLOSURE

The present inventors have surprisingly identified that treatment of inflammatory lung diseases can be achieved in subjects with elevated baseline levels of circulating C-reactive protein (CRP), by administering mesenchymal lineage precursor or stem cells (MLPSCs). These findings suggest a strategy for stratification of patients with inflammatory lung disease for treatment with MLPSCs.

Accordingly, in a first example, the present disclosure relates to a method of treating or preventing inflammatory lung disease in a human subject in need thereof, the method comprising administering to the subject a composition comprising mesenchymal lineage precursor or stem cells (MLPSCs), wherein the subject has an elevated circulating C-reactive protein (CRP). In an example, the subject has an initial circulating CRP level of at least 2 mg/ml. In another example, the subject has an initial circulating CRP level of at least 3 mg/ml. In another example, the subject has an initial circulating CRP level of at least 3 mg/ml or at least 4 mg/ml. In another example, the subject has an initial circulating CRP level of at least 4 mg/ml.

In one example, wherein the inflammatory lung disease is selected from the group consisting of Acute Respiratory Distress Syndrome (ARDS), Chronic Obstructive Pulmonary Disease (COPD), Idiopathic Pulmonary Fibrosis (IPF), Pulmonary Arterial Hypertension (PAH), asthma, cystic fibrosis, pneumonia, interstitial lung diseases or one or more thereof.

In another example, the inflammatory lung disease is caused by a viral infection. The viral infection may be caused, for example, by a rhinovirus, influenza virus, respiratory syncytial virus (RSV) or a coronavirus.

In one example, the inflammatory lung disease is caused by a coronavirus infection. The coronavirus may be Severe Acute Respiratory Syndrome coronavirus (SARS-CoV), Middle East Respiratory Syndrome coronavirus (MERS-CoV), COVID-19, 229E, NL63, OC43, or KHU1. In one example, the coronavirus is SARS-CoV, MERS-CoV or COVID-19.

In an example, subjects treated according to the present disclosure are infected with a virus and have a circulating CRP level of at least 4 mg/ml. In another example, subjects treated according to the present disclosure are infected with a virus and have a circulating CRP level between 2 and 6 mg/ml. For example, subjects may be infected with a rhinovirus, influenza virus, respiratory syncytial virus (RSV) or a coronavirus and have a circulating CRP level of at least 4 mg/ml. In another example, subjects may be infected with a coronavirus and have a circulating CRP level of at least 4 mg/ml. For example, subjects may be infected with Severe Acute Respiratory Syndrome coronavirus (SARS-CoV), Middle East Respiratory Syndrome coronavirus (MERS-CoV), COVID-19, 229E, NL63, OC43, or KHU1 and have a circulating CRP level of at least 4 mg/ml. In another example, subjects may be infected with SARS-CoV, MERS-CoV or COVID-19 and have a circulating CRP level of at least 4 mg/ml.

In another example, the methods of the present disclosure comprise the steps of: i) selecting a subject with an inflammatory lung disease who has a circulating CRP level of greater than or equal to 4 mg/L, and ii) administering to the subject a composition comprising mesenchymal lineage precursor or stem cells (MLPSCs).

In an example, the MLPSCs have been cryopreserved and thawed. In an example, the MLPSCs are culture expanded from an intermediate cryopreserved MLPSCs population. In another example, the MLPSCs are culture expanded for at least about 5 passages. In an example, the MLPSCs express at least 13 pg TNFR1 per million MLPSCs. In an example, the MLPSCs express about 13 pg to about 44 pg TNFR1 per million MLPSCs. In an example, culture expanded MLPSCs are culture expanded for at least 20 population doublings. In another example, culture expanded MLPSCs are culture expanded for at least 30 population doublings. In an example, the MLPSCs are mesenchymal stem cells (MSCs). In another example, the MLPSCs are allogeneic. For example, the MLPSCs may be allogeneic MSCs.

In an example, the composition is administered intravenously.

In an example, the methods of the disclosure encompass administering between $1 \times 10^7$ and $2 \times 10^8$ cells. For example, multiple doses of between $1 \times 10^7$ and $2 \times 10^8$ cells may be administered on days 0, 30, 60 and 90. In an example, the methods of the disclosure encompass administering about $1 \times 10^8$ cells per dose. In an example, a dose is administered at baseline followed by 3 subsequent doses monthly over 90 days.

In an example, the subject has an improvement in FEV1 after treatment. In an example, the subject has an FEV1 change from baseline of at least 0.02, or at least 0.05, within 120 days of receiving the first dose of cells. In an example, the subject has an FEV1 change from baseline of at least 0.05, within 120 days of receiving the first dose of cells. In an example, the subject has an improvement in FVC after treatment. In an example, the subject has an FVC change from baseline of at least 0.05, or at least 0.1, within 120 days of receiving the first dose of cells. In an example, the subject has an improvement in FEV1/FVC after treatment. In another example, the subject has an FEV1/FVC change from baseline of at least 0.01, or at least 0.015, within 120 days of receiving the first dose of cells. In another example, the subject has an FEV1/FVC change from baseline of at least 0.01, or at least 0.015, within 150 days of receiving the first dose of cells. In an example, the subject shows an improvement in a 6 minute walk test after treatment. In an example, the subject shows an improvement in the 6 minute walk test of at least 40 meters, or at least 50 meters, within 60 days of receiving the first dose of cells. In an example, the subject shows an improvement in the 6 minute walk test of at least 40 meters, or at least 50 meters, within 120 days of receiving the first dose of cells. In an example, the subject shows an improvement in FEV1, FVC and 6 minute walk test within 120 days of receiving the first dose of cells.

In an example, the subject shows an improvement in FEV1 and FVC within 120 days of receiving the first dose of cells. In an example, the subject shows an improvement in FEV1, FVC and the 6 minute walk test within 120 days of receiving the first dose of cells. In an example, the subject shows an improvement in FVC within 120 days of receiving the first dose of cells. In another example, the composition further comprises Plasma-Lyte A, dimethyl sulfoxide (DMSO), human serum albumin (HSA). In an example, the composition further comprises Plasma-Lyte A (70%), DMSO (10%), HSA (25%) solution, the HSA solution comprising 5% HSA and 15% buffer.

In an example, the composition comprises greater than $6.68 \times 10^6$ viable cells/mL.

BRIEF DESCRIPTION OF ACCOMPANYING FIGURES

Figure 2:
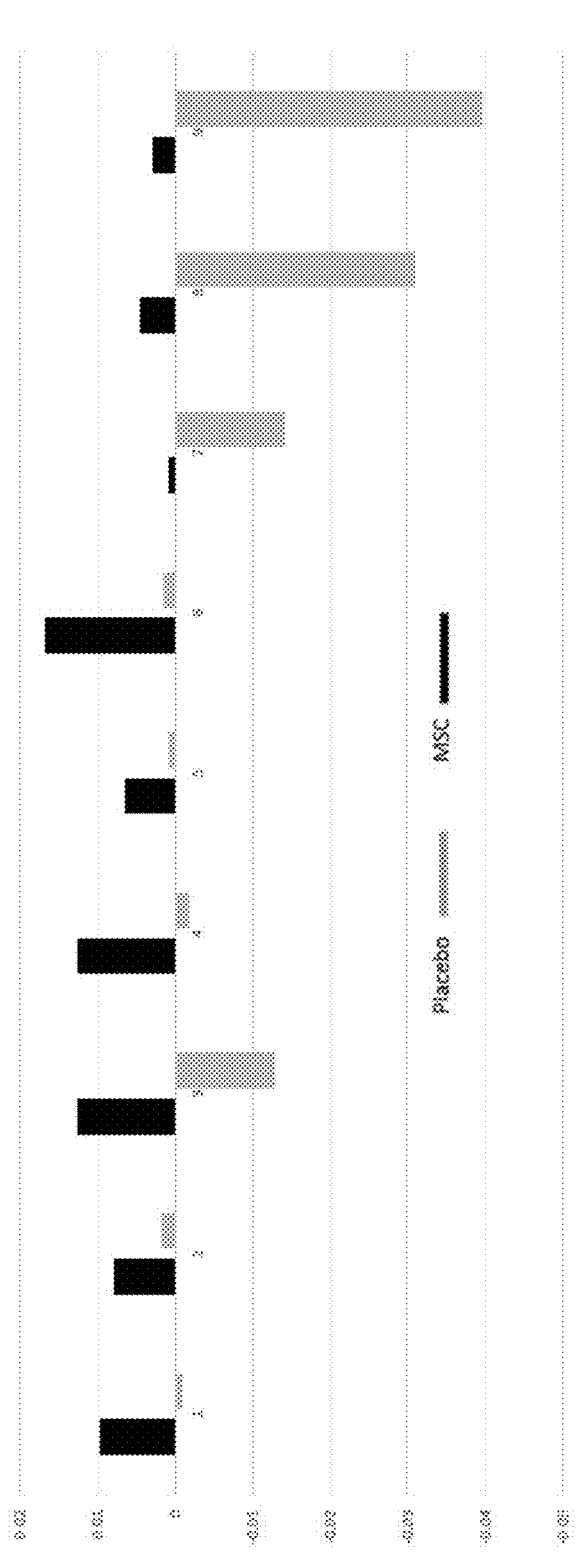
Figure 3:
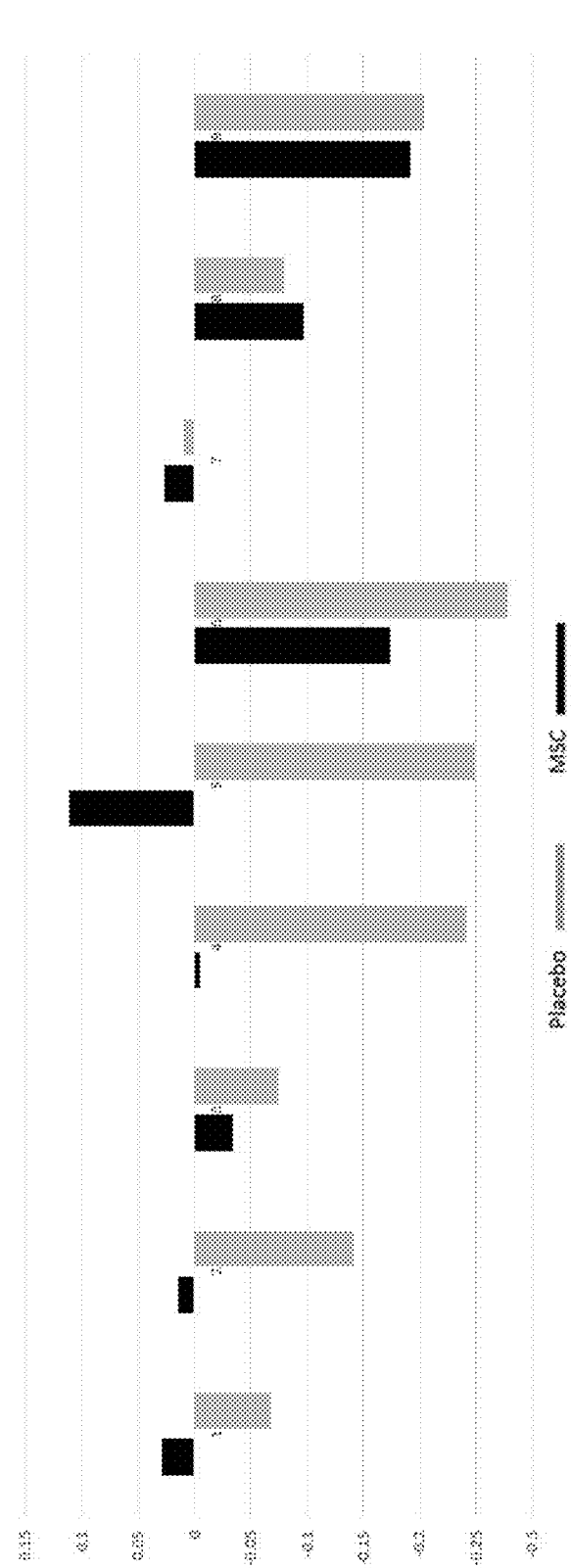
Figure 4:
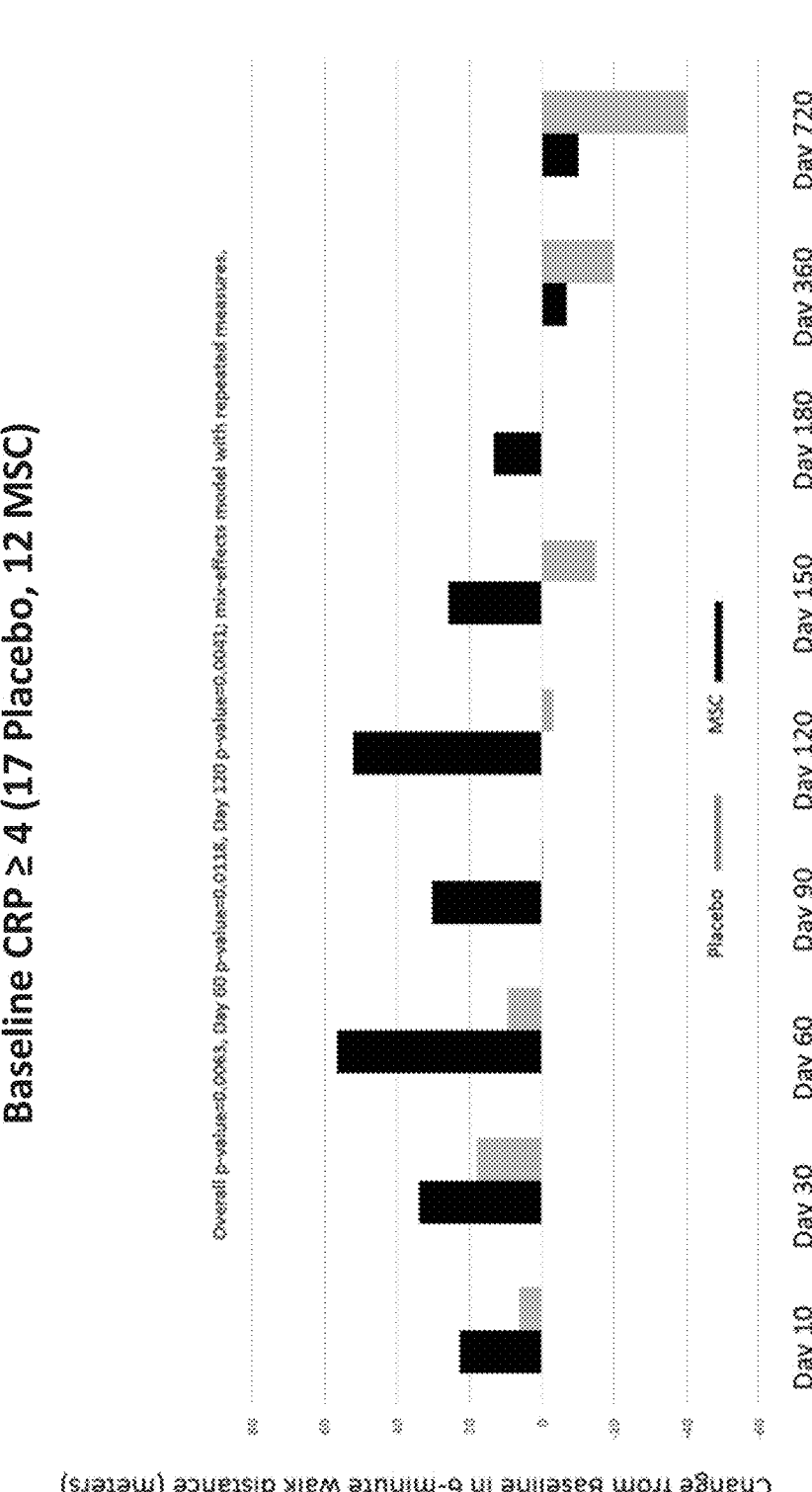

FIG. 1: FEV1 Change from BL (L) (CRP≥4 mg/ml).
FIG. 2: Change from BL in FEV1/FVC (CRP≥4 mg/ml).
FIG. 3: FVC Change from BL High (CRP≥4 mg/ml).
FIG. 4: Change from BL total 6 MW distance (Meters) (CRP≥4 mg/ml).

DETAILED DESCRIPTION

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure, as described herein.

Any example disclosed herein shall be taken to apply mutatis mutandis to any other example unless specifically stated otherwise.

Unless specifically defined otherwise, all technical and scientific terms used herein shall be taken to have the same meaning as commonly understood by one of ordinary skill in the art (e.g., in cell culture, molecular genetics, stem cell differentiation, immunology, immunohistochemistry, protein chemistry, and biochemistry).

Unless otherwise indicated, the surgical techniques utilized in the present disclosure are standard procedures, well known to those skilled in the art.

Methods of obtaining and enriching a population of mesenchymal lineage stem or precursor cells are known in the art. For example, enriched populations of mesenchymal lineage stem or precursor cells can be obtained by the use of flow cytometry and cell sorting procedures based on the use of cell surface markers that are expressed on mesenchymal lineage stem or precursor cells.

All documents cited or referenced herein, and all documents cited or referenced in herein cited documents, together with any manufacturer's instructions, descriptions, product specifications, and product sheets for any products mentioned herein or in any document incorporated by reference herein, are hereby incorporated herein by reference in their entirety.

Selected Definitions

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the singular form "a", "an" and "the" include singular and plural references unless the context indicates otherwise.

By "isolated" or "purified" it is meant a cell which has been separated from at least some components of its natural environment. This term includes gross physical separation of the cells from its natural environment (e.g. removal from a donor). The term "isolated" includes alteration of the cell's relationship with the neighboring cells with which it is in direct by, for example, dissociation. The term "isolated" does not refer to a cell which is in a tissue section. When used to refer to the population of cells, the term "isolated" includes populations of cells which result from proliferation of the isolated cells of the disclosure.

The terms "passage", "passaging" or "sub-culture" are used in the context of the present disclosure to refer to known cell culture techniques that are used to keep cells alive and growing under cultured conditions for extended periods of time so that cell numbers can continually increase. The degree of sub-culturing a cell line has undergone is often expressed as "passage number," which is generally used to refer to the number of times cells have been sub-cultured. In an example, one passage comprises removing non-adherent cells and leaving adherent mesenchymal lineage precursor or stem cells. Such mesenchymal lineage precursor or stem cells can then be dissociated from the substrate or flask (e.g., by using a protease such as trypsin or collagenase), media can be added, optional washing (e.g., by centrifugation) may be performed, and then the mesenchymal lineage precursor or stem cells can be re-plated or reseeded to one or more culture vessels containing a greater surface area in total. The mesenchymal lineage precursor or stem cells can then continue to expand in culture. In another example, methods of removing non-adherent cells include steps of non-enzymatic treatment (e.g., with EDTA). In an example, mesenchymal lineage precursor or stem cells are passaged at or near confluence (e.g., about 75% to about 95% confluence). In an example, the mesenchymal lineage precursor or stem cells are seeded at a concentration of about 10%, about 15%, or about 20% cells/ml of culture medium.

The term "medium" or "media" as used in the context of the present disclosure, includes the components of the environment surrounding cells in culture. It is envisaged that the media contributes to and/or provides the conditions suitable to allow cells to grow. Media may be solid, liquid, gaseous or a mixture of phases and materials. Media can include liquid growth media as well as liquid media that do not sustain cell growth. Exemplary gaseous media include the gaseous phase that cells growing on a petri dish or other solid or semisolid support are exposed to.

As used herein, the terms "treating", "treat" or "treatment" include administering a population of mesenchymal lineage stem or precursor cells and/or progeny thereof and/or soluble factors derived therefrom to thereby reduce or eliminate at least one symptom of inflammatory lung disease. In an example, treatment includes administering a population of culture expanded mesenchymal lineage stem or precursor cells. In an example, treatment response is determined relative to baseline.

In an example, treatment is determined based on a subjects spirometry measurements. In an example, spirometry measurements are determined based on American Association for Respiratory Care (AARC) Spirometry Clinical Practice Guideline (American Association for Respiratory Care: AARC clinical practice guideline: Spirometry, 1996 Update., Respir Care., 41:629-638).

In an example, treatment improves a subjects FEV1. In an example, the improvement in FEV1 is observed as change from baseline of at least 0.02, or at least 0.05. In another example, the improvement in FEV1 is observed as change from baseline of between 0.02 and 0.06. In another example, the improvement in FEV1 is observed as change from baseline of between 0.02 and 0.05. In an example, an above referenced improvement in FEV1 is observed within 120 days, 150 days or 180 days of receiving the first dose of cells. In an example, an above referenced improvement in FEV1 is observed after receiving four doses of cells over three months. In an example, an above referenced improvement in FEV1 is observed after receiving a total dose of 400 million cells.

In an example, treatment improves a subjects FVC. In an example, the improvement in FVC is observed as change from baseline of at least 0.05, or at least 0.1. In another example, the improvement in FVC is observed as change from baseline of between 0.05 and 0.15. In another example, the improvement in FVC is observed as change from baseline of between 0.05 and 0.1. In an example, an above referenced improvement in FVC is observed within 120 days or 150 days of receiving the first dose of cells. In an example, an above referenced improvement in FVC is observed after receiving four doses of cells over three months. In an example, an above referenced improvement in FVC is observed after receiving a total dose of 400 million cells.

In another example, treatment improves a subjects FEV1/FVC. In an example, the improvement in FEV1/FVC is observed as change from baseline of at least 0.007, or at least 0.013. In another example, the improvement in FEV1/FVC is observed as change from baseline of between 0.007 and 0.014. In another example, the improvement in FEV1/FVC is observed as change from baseline of between 0.007 and 0.014. In an example, an above referenced improvement in FEV1/FVC is observed within 120 days, 150 days or 180 days of receiving the first dose of cells. In an example, an above referenced improvement in FEV1/FVC is observed after receiving four doses of cells over three months. In an example, an above referenced improvement in FEV1/FVC is observed after receiving a total dose of 400 million cells.

In another example, treatment improves a subjects 6 minute walk test. In an example, the improvement in 6 minute walk test is at least 40 meters, or at least 50 meters. In an example, the improvement in 6 minute walk test is between 40 and 60 meters. In an example, the improvement in 6 minute walk test is between 40 and 50 meters. In an example, an above referenced improvement in 6 minute walk test is observed within 60 days or 90 days of receiving the first dose of cells. In an example, an above referenced improvement in 6 minute walk test is observed after receiving two doses of cells over two months. In an example, an above referenced improvement in 6 minute walk test is observed within 120 days or 150 days of receiving the first dose of cells. In an example, an above referenced improvement in 6 minute walk test is observed after receiving four doses of cells over three months. In an example, an above referenced improvement in 6 minute walk test is observed after receiving a total dose of 400 million cells.

In an example, 6 minute walk test results are determined based on ATS statement: guidelines for the six-minute walk test (2002) Am J Respir Crit Care Med., 166:111-7.

The term "prevent" or "preventing" as used herein include administering a population of mesenchymal lineage stem or precursor cells and/or progeny thereof and/or soluble factors derived therefrom to thereby stop or inhibit the development of at least one symptom of an inflammatory lung disease disclosed herein.

The term "inflammatory lung disease" is used in the context of the present disclosure refer to diseases which result from ongoing inflammatory process in the airway and/or lungs. For example, COPD is inflammatory lung disease where both the airways and lung tissue are affected. This can manifest as a combination of chronic obstructive bronchitis and emphysema, where the former is the result of chronic inflammation of the bronchial tubes and the latter is due to breakdown of the alveoli. Other examples of inflammatory lung diseases include Acute Respiratory Distress Syndrome (ARDS), Idiopathic Pulmonary Fibrosis (IPF), Pulmonary Arterial Hypertension (PAH), asthma, cystic fibrosis, pneumonia and interstitial lung diseases. In an example, the inflammatory lung disease is caused by a viral infection. For example, the inflammatory lung disease can be caused by a rhinovirus, an influenza virus, a respiratory syncytial virus (RSV) or a coronavirus. In an example, the inflammatory lung disease can be caused by a coronavirus. For example, the coronavirus can be coronavirus (SARS-CoV), Middle East Respiratory Syndrome coronavirus (MERS-CoV) or COVID-19. In an example, the inflammatory lunch disease is characterized by a combination of the above referenced indications. For example, the inflammatory lung disease may comprise COPD and ARDS.

"C-reactive protein" or "CRP" is an inflammatory mediator whose levels are raised under conditions of acute inflammatory recurrence and rapidly normalize once the inflammation subsides. In an example, subjects treated according to the present disclosure have elevated circulating CRP levels. The term "elevated circulating CRP level" is used in the context of the present disclosure to refer to subjects with symptom(s) of inflammatory lung disease and a circulating CRP level >1 mg/ml. In an example, the subject with elevated circulating CRP levels can be diagnosed with an inflammatory lung disease and have a circulating CRP level >1 mg/ml.

In an example, subjects treated according to the present disclosure have an initial circulating CRP level ≥1.5 mg/ml. In another example, subjects treated according to the present disclosure have an initial circulating CRP level ≥2 mg/ml. In an example, subjects treated according to the present disclosure have an initial circulating CRP level ≥3 mg/ml. In an example, subjects treated according to the present disclosure have an initial circulating CRP level ≥3.5 mg/ml. In another example, subjects have an initial circulating CRP level ≥4 mg/ml. In another example, subjects have an initial circulating CRP level ≥5 mg/ml, ≥6 mg/ml, ≥7 mg/ml, ≥8 mg/ml, ≥9 mg/ml, ≥10 mg/ml. In an example, subjects have an initial circulating CRP level between 2 mg/ml and 10 mg/ml. In another example, subjects have an initial circulating CRP level between 3 mg/ml and 10 mg/ml. In another example, subjects have an initial circulating CRP level between 2 mg/ml and 15 mg/ml. In another example, subjects have an initial circulating CRP level between 2 mg/ml and 20 mg/ml.

In an example, methods of the present disclosure inhibit disease progression or disease complication in a subject. "Inhibition" of disease progression or disease complication in a subject means preventing or reducing the disease progression and/or disease complication in the subject.

The term "subject" as used herein refers to a human subject. For example, the subject can be an adult. In another example, the subject can be a child. In another example, the subject can be an adolescent. Terms such as "subject", "patient" or "individual" are terms that can, in context, be used interchangeably in the present disclosure.

Subjects treated according to the present disclosure may have symptoms indicative of an inflammatory lung disease and an initial circulating CRP level ≥4 mg/ml. Exemplary symptoms indicative of an inflammatory lung disease include fatigue, trouble breathing, shortness of breath, inability or decreased ability to exercise, coughing with or without blood or mucus, pain when breathing in or out, wheezing, chest tightness, unexplained weight loss, and musculoskeletal pain. In an example, inflammatory lung disease is diagnosed based on lung function testing. For example, inflammatory lung disease can be diagnosed based on one or more of forced vital capacity (FVC), forced expiratory volume in one second (FEV1) and forced expiratory flow (FEF). In an example, inflammatory lung disease is diagnosed based on FEV1/FVC ratio.

In another example, the subject is 18-75 years of age. In another example, the subject has COPD. In another example, the subject has ARDS. In another example, the subject has IPF. In another example, the subject has PAH. In another example, the subject has asthma. In another example, the subject has cystic fibrosis. In another example, the subject has pneumonia. In another example, the subject has interstitial lung diseases. In another example, the subject has a combination thereof such as COPD and ARDS.

In another example, the subject has ARDS secondary to viral infection. In an example, the subjects ARDS is secondary to infection with a rhinovirus, an influenza virus, a respiratory syncytial virus (RSV) or a coronavirus. In an example, the subjects ARDS is secondary to infection with a coronavirus. For example, the subjects ARDS can be secondary to infection with SARS-CoV, MERS-CoV or COVID-19.

In another example, the methods of the present disclosure prevent or treat subjects with mild COPD. In another example, the methods of the present disclosure prevent or treat subjects with moderate COPD. In another example, the methods of the present disclosure prevent or treat subjects with severe COPD. In another example, the methods of the present disclosure prevent or treat subjects with very severe COPD. In another example, the methods of the present disclosure prevent or treat subjects with moderate or severe COPD. In another example, the methods of the present disclosure prevent or treat subjects with moderate, severe or very severe COPD. In an example, the severity of COPD is determined based on Global Initiative for Obstructive Lung Disease (GOLD) criteria for COPD (see for example, Rabe et al., (2007) Respir Crit Care Med., 176:532-555). In this example, subjects with COPD can have an FEV1/FVC ratio of <0.70. In an example, in subjects with an FEV1/FVC ratio of <0.70 the following is used to diagnose the severity of COPD:

GOLD 1—mild: FEV1≥80% predicted;
GOLD 2—moderate: 50%≤FEV1<80% predicted;
GOLD 3—severe: 30%≤FEV1<50% predicted;
GOLD 4—very severe: FEV1<30% predicted.

As used herein, the term "genetically unmodified" refers to cells that have not been modified by transfection with a nucleic acid. For the avoidance of doubt, in the context of the present disclosure a mesenchymal lineage precursor or stem cell transfected with a nucleic acid encoding Ang1 would be considered genetically modified.

The term "total dose" is used in the context of the present disclosure to refer to the total number of cells received by the subject treated according to the present disclosure. In an example, the total dose consists of one administration of cells. In another example, the total dose consists of two administrations of cells. In another example, the total dose consists of three administrations of cells. In another example, the total dose consists of four or more administrations of cells. For example, the total dose can consist of two to four administrations of cells.

Mesenchymal Lineage Precursor Cells

As used herein, the term "mesenchymal lineage precursor or stem cell (MLPSC)" refers to undifferentiated multipotent cells that have the capacity to self-renew while maintaining multipotency and the capacity to differentiate into a number of cell types either of mesenchymal origin, for example, osteoblasts, chondrocytes, adipocytes, stromal cells, fibroblasts and tendons, or non-mesodermal origin, for example, hepatocytes, neural cells and epithelial cells. For the avoidance of doubt, a "mesenchymal lineage precursor cell" refers to a cell which can differentiate into a mesenchymal cell such as bone, cartilage, muscle and fat cells, and fibrous connective tissue.

The term "mesenchymal lineage precursor or stem cells" includes both parent cells and their undifferentiated progeny. The term also includes mesenchymal precursor cells, multipotent stromal cells, mesenchymal stem cells (MSCs), perivascular mesenchymal precursor cells, and their undifferentiated progeny.

Mesenchymal lineage precursor or stem cells can be autologous, allogeneic, xenogenic, syngenic or isogenic. Autologous cells are isolated from the same individual to which they will be reimplanted. Allogeneic cells are isolated from a donor of the same species. Xenogenic cells are isolated from a donor of another species. Syngenic or isogenic cells are isolated from genetically identical organisms, such as twins, clones, or highly inbred research animal models.

In an example, the mesenchymal lineage precursor or stem cells are allogeneic. In an example, the allogeneic mesenchymal lineage precursor or stem cells are culture expanded and cryopreserved.

Mesenchymal lineage precursor or stem cells reside primarily in the bone marrow, but have also shown to be present in diverse host tissues including, for example, cord blood and umbilical cord, adult peripheral blood, adipose tissue, trabecular bone and dental pulp. They are also found in skin, spleen, pancreas, brain, kidney, liver, heart, retina, brain, hair follicles, intestine, lung, lymph node, dermis, ligament, tendon, skeletal muscle, dermis, and periosteum; and are capable of differentiating into germ lines such as mesoderm and/or endoderm and/or ectoderm. Thus, mesenchymal lineage precursor or stem cells are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues.

The terms "enriched", "enrichment" or variations thereof are used herein to describe a population of cells in which the proportion of one particular cell type or the proportion of a number of particular cell types is increased when compared with an untreated population of the cells (e.g., cells in their native environment). In one example, a population enriched for mesenchymal lineage precursor or stem cells comprises at least about 0.1% or 0.5% or 1% or 2% or 5% or 10% or 15% or 20% or 25% or 30% or 50% or 75% mesenchymal lineage precursor or stem cells. In this regard, the term "population of cells enriched for mesenchymal lineage precursor or stem cells" will be taken to provide explicit support for the term "population of cells comprising X % mesenchymal lineage precursor or stem cells", wherein X % is a percentage as recited herein. The mesenchymal lineage precursor or stem cells can, in some examples, form clonogenic colonies, e.g. CFU-F (fibroblasts) or a subset thereof (e.g., 50% or 60% or 70% or 70% or 90% or 95%) can have this activity.

In an example of the present disclosure, the mesenchymal lineage precursor or stem cells are mesenchymal stem cells (MSCs). The MSCs may be a homogeneous composition or may be a mixed cell population enriched in MSCs. Homogeneous MSC compositions may be obtained by culturing adherent marrow or periosteal cells, and the MSCs may be identified by specific cell surface markers which are identified with unique monoclonal antibodies. A method for obtaining a cell population enriched in MSCs is described, for example, in U.S. Pat. No. 5,486,359. Alternative sources for MSCs include, but are not limited to, blood, skin, cord blood, muscle, fat, bone, and perichondrium. In an example, the MSCs are allogeneic. In an example, the MSCs are cryopreserved. In an example, the MSCs are culture expanded and cryopreserved.

In another example, the mesenchymal lineage precursor or stem cells are CD29+, CD54+, CD73+, CD90+, CD102+, CD105+, CD106+, CD166+, MHC1+ MSCs.

Isolated or enriched mesenchymal lineage precursor or stem cells can be expanded in vitro by culture. Isolated or enriched mesenchymal lineage precursor or stem cells can be cryopreserved, thawed and subsequently expanded in vitro by culture.

In one example, isolated or enriched mesenchymal lineage precursor or stem cells are seeded at 50,000 viable cells/$cm^2$ in culture medium (serum free or serum-supplemented), for example, alpha minimum essential media ($\alpha$MEM) supplemented with 5% fetal bovine serum (FBS) and glutamine, and allowed to adhere to the culture vessel overnight at 37° C., 20% $O_2$. The culture medium is subsequently replaced and/or altered as required and the cells cultured for a further 68 to 72 hours at 37° C., 5% $O_2$.

As will be appreciated by those of skill in the art, cultured mesenchymal lineage precursor or stem cells are phenotypically different to cells in vivo. For example, in one embodiment they express one or more of the following markers, CD44, NG2, DC146 and CD140b. Cultured mesenchymal lineage precursor or stem cells are also biologically different to cells in vivo, having a higher rate of proliferation compared to the largely non-cycling (quiescent) cells in vivo.

In one example, the population of cells is enriched from a cell preparation comprising STRO-1+ cells in a selectable form. In this regard, the term "selectable form" will be understood to mean that the cells express a marker (e.g., a cell surface marker) permitting selection of the STRO-1+ cells. The marker can be STRO-1, but need not be. For example, as described and/or exemplified herein, cells (e.g., mesenchymal precursor cells) expressing STRO-2 and/or STRO-3 (TNAP) and/or STRO-4 and/or VCAM-1 and/or CD146 and/or 3G5 also express STRO-1 (and can be STRO-1 bright). Accordingly, an indication that cells are STRO-1+ does not mean that the cells are selected solely by STRO-1 expression. In one example, the cells are selected based on at least STRO-3 expression, e.g., they are STRO-3+ (TNAP+).

Reference to selection of a cell or population thereof does not necessarily require selection from a specific tissue source. As described herein STRO-1+ cells can be selected from or isolated from or enriched from a large variety of sources. That said, in some examples, these terms provide support for selection from any tissue comprising STRO-1+ cells (e.g., mesenchymal precursor cells) or vascularized tissue or tissue comprising pericytes (e.g., STRO-1+ pericytes) or any one or more of the tissues recited herein.

In one example, the cells used in the present disclosure express one or more markers individually or collectively selected from the group consisting of TNAP+, VCAM-1+, THY-1+, STRO-2+, STRO-4+ (HSP-90$\beta$), CD45+, CD146+, 3G5+ or any combination thereof.

By "individually" is meant that the disclosure encompasses the recited markers or groups of markers separately, and that, notwithstanding that individual markers or groups of markers may not be separately listed herein the accompanying claims may define such marker or groups of markers separately and divisibly from each other.

By "collectively" is meant that the disclosure encompasses any number or combination of the recited markers or groups of markers, and that, notwithstanding that such numbers or combinations of markers or groups of markers may not be specifically listed herein the accompanying claims may define such combinations or sub-combinations separately and divisibly from any other combination of markers or groups of markers.

As used herein the term "TNAP" is intended to encompass all isoforms of tissue non-specific alkaline phosphatase. For example, the term encompasses the liver isoform (LAP), the bone isoform (BAP) and the kidney isoform (KAP). In one example, the TNAP is BAP. In one example, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in one example, the STRO-1+ cells are capable of giving rise to clonogenic CFU-F.

In one example, a significant proportion of the STRO-1+ cells are capable of differentiation into at least two different germ lines. Non-limiting examples of the lineages to which the STRO-1+ cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In an example, mesenchymal lineage precursor or stem cells are obtained from a single donor, or multiple donors where the donor samples or mesenchymal lineage precursor or stem cells are subsequently pooled and then culture expanded.

Mesenchymal lineage precursor or stem cells encompassed by the present disclosure may also be cryopreserved prior to administration to a subject. In an example, mesenchymal lineage precursor or stem cells are culture expanded and cryopreserved prior to administration to a subject.

In an example, the present disclosure encompasses mesenchymal lineage precursor or stem cells as well as progeny thereof, soluble factors derived therefrom, and/or extracellular vesicles isolated therefrom. In another example, the present disclosure encompasses mesenchymal lineage precursor or stem cells as well as extracellular vesicles isolated therefrom. For example, it is possible to culture expand mesenchymal precursor lineage or stem cells of the disclosure for a period of time and under conditions suitable for secretion of extracellular vesicles into the cell culture medium. Secreted extracellular vesicles can subsequently be obtained from the culture medium for use in therapy.

The term "extracellular vesicles" as used herein, refers to lipid particles naturally released from cells and ranging in size from about 30 nm to as a large as 10 microns, although typically they are less than 200 nm in size. They can contain proteins, nucleic acids, lipids, metabolites, or organelles from the releasing cells (e.g., mesenchymal stem cells; STRO-1$^+$ cells).

The term "exosomes" as used herein, refers to a type of extracellular vesicle generally ranging in size from about 30 nm to about 150 nm and originating in the endosomal compartment of mammalian cells from which they are trafficked to the cell membrane and released. They may contain nucleic acids (e.g., RNA; microRNAs), proteins, lipids, and metabolites and function in intercellular communication by being secreted from one cell and taken up by other cells to deliver their cargo.

Culture Expansion of the Cells

In an example, mesenchymal lineage precursor or stem cells are culture expanded. "Culture expanded" mesenchymal lineage precursor or stem cells media are distinguished from freshly isolated cells in that they have been cultured in cell culture medium and passaged (i.e. sub-cultured). In an example, culture expanded mesenchymal lineage precursor or stem cells are culture expanded for about 4-10 passages. In an example, mesenchymal lineage precursor or stem cells are culture expanded for at least 5, at least 6, at least 7, at least 8, at least 9, at least 10 passages. For example, mesenchymal lineage precursor or stem cells can be culture expanded for at least 5 passages. In an example, mesenchymal lineage precursor or stem cells can be culture expanded for at least 5-10 passages. In an example, mesenchymal lineage precursor or stem cells can be culture expanded for at least 5-8 passages. In an example, mesenchymal lineage precursor or stem cells can be culture expanded for at least 5-7 passages. In an example, mesenchymal lineage precursor or stem cells can be culture expanded for more than 10 passages. In another example, mesenchymal lineage precursor or stem cells can be culture expanded for more than 7 passages. In these examples, stem cells may be culture expanded before being cryopreserved to provide an intermediate cryopreserved MLPSC population. In an example, compositions of the disclosure are prepared from an intermediate cryopreserved MLPSC population. For example, an intermediate cryopreserved MLPSC population can be further culture expanded prior to administration as is discussed further below. Accordingly, in an example, mesenchymal lineage precursor or stem cells are culture expanded and cryopreserved. In an embodiment of these examples, mesenchymal lineage precursor or stem cells can be obtained from a single donor, or multiple donors where the donor samples or mesenchymal lineage precursor or stem cells are subsequently pooled and then culture expanded. In an example, the culture expansion process comprises:

i. expanding by passage expansion the number of viable cells to provide a preparation of at least about 1 billion of the viable cells, wherein the passage expansion comprises establishing a primary culture of isolated mesenchymal lineage precursor or stem cells and then serially establishing a first non-primary (P1) culture of isolated mesenchymal lineage precursor or stem cells from the previous culture;

ii. expanding by passage expansion the P1 culture of isolated mesenchymal lineage precursor or stem cells to a second non-primary (P2) culture of mesenchymal lineage precursor or stem cells; and, iii. preparing and cryopreserving an in-process intermediate mesenchymal lineage precursor or stem cells preparation obtained from the P2 culture of mesenchymal lineage precursor or stem cells; and, iv. thawing the cryopreserved in-process intermediate mesenchymal lineage precursor or stem cells preparation and expanding by passage expansion the in-process intermediate mesenchymal lineage precursor or stem cells preparation.

In an example, the expanded mesenchymal lineage precursor or stem cell preparation has an antigen profile and an activity profile comprising:

i. less than about 0.75% CD45+ cells;

ii. at least about 95% CD105+ cells;

iii. at least about 95% CD166+ cells.

In an example, the expanded mesenchymal lineage precursor or stem cell preparation is capable of inhibiting IL2Ra expression by CD3/CD28-activated PBMCs by at least about 30% relative to a control.

In an example, culture expanded mesenchymal lineage precursor or stem cells are culture expanded for about 4-10 passages, wherein the mesenchymal lineage precursor or stem cells have been cryopreserved after at least 2 or 3 passages before being further culture expanded. In an example, mesenchymal lineage precursor or stem cells are culture expanded for at least 1, at least 2, at least 3, at least 4, at least 5 passages, cryopreserved and then further culture expanded for at least 1, at least 2, at least 3, at least 4, at least 5 passages before being administered or further cryopreserved.

In an example, the majority of mesenchymal lineage precursor or stem cells in compositions of the disclosure are of about the same generation number (i.e., they are within about 1 or about 2 or about 3 or about 4 cell doublings of each other). In an example, the average number of cell doublings in the present compositions is about 20 to about 25 doublings. In an example, the average number of cell doublings in the present compositions is about 9 to about 13 (e.g., about 11 or about 11.2) doublings arising from the primary culture, plus about 1, about 2, about 3, or about 4 doublings per passage (for example, about 2.5 doublings per passage). Exemplary average cell doublings in present compositions are any of about 13.5, about 16, about 18.5, about 21, about 23.5, about 26, about 28.5, about 31, about 33.5, and about 36 when produced by about 1, about 2, about 3, about 4, about 5, about 6, about 7, about 8, about 9, and about 10 passages, respectively.

The process of mesenchymal lineage precursor or stem cell isolation and ex vivo expansion can be performed using any equipment and cell handing methods known in the art. Various culture expansion embodiments of the present disclosure employ steps that require manipulation of cells, for example, steps of seeding, feeding, dissociating an adherent culture, or washing. Any step of manipulating cells has the potential to insult the cells. Although mesenchymal lineage precursor or stem cells can generally withstand a certain amount of insult during preparation, cells are preferably manipulated by handling procedures and/or equipment that adequately performs the given step(s) while minimizing insult to the cells.

In an example, mesenchymal lineage precursor or stem cells are washed in an apparatus that includes a cell source bag, a wash solution bag, a recirculation wash bag, a spinning membrane filter having inlet and outlet ports, a filtrate bag, a mixing zone, an end product bag for the washed cells, and appropriate tubing, for example, as described in U.S. Pat. No. 6,251,295, which is hereby incorporated by reference.

In an example, a mesenchymal lineage precursor or stem cell composition according to the present disclosure is 95% homogeneous with respect to being CD105 positive and CD166 positive and being CD45 negative. In an example, this homogeneity persists through ex vivo expansion; i.e. though multiple population doublings. In an example, the composition comprises at least one therapeutic dose of mesenchymal lineage precursor or stem cells and the mesenchymal lineage precursor or stem cells comprise less than about 1.25% CD45+ cells, at least about 95% CD105+ cells, and at least about 95% CD166+ cells. In an example, this homogeneity persists after cryogenic storage and thawing, where the cells also generally have a viability of about 70% or more.

In an example, compositions of the disclosure comprise mesenchymal lineage precursor or stem cells which express substantial levels of TNFR1, for example greater than 13 pg of TNFR1 per million mesenchymal lineage precursor or stem cells. In an example, this phenotype is stable throughout ex vivo expansion and cryogenic storage. In an example, expression of levels of TNFR1 in the range of about 13 to about 179 pg (e.g. about 13 pg to about 44 pg) per million mesenchymal lineage precursor or stem cells is associated with a desirous therapeutic potential which also persists through ex vivo expansion and cryopreservation.

In an example, the culture expanded mesenchymal lineage precursor or stem cells express Tumor necrosis factor receptor 1 (TNFR1) in an amount of at least 110 pg/ml. For example, the mesenchymal lineage precursor or stem cells can express TNFR1 in an amount of at least 150 pg/ml, or at least 200 pg/ml, or at least 250 pg/ml, or at least 300 pg/ml, or at least 320 pg/ml, or at least 330 pg/ml, or at least 340 pg/ml, or at least 350 pg/ml.

In an example, the mesenchymal lineage precursor or stem cells express TNFR1 in an amount of at least 13 pg/$10^6$ cells. For example, the mesenchymal lineage precursor or stem cells express TNFR1 in an amount of at least 15 pg/$10^6$ cells, or at least 20 pg/$10^6$ cells, or at least 25 pg/$10^6$ cells, or at least 30 pg/$10^6$ cells, or at least 35 pg/$10^6$ cells, or at least 40 pg/$10^6$ cells, or at least 45 pg/$10^6$ cells, or at least 50 pg/$10^6$ cells.

In another example, mesenchymal lineage precursor or stem cells disclosed herein inhibit IL-2Rα expression on T-cells. In an example, mesenchymal lineage precursor or stem cells can inhibit IL-2Rα expression by at least about 30%, alternatively at least about 35%, alternatively at least about 40%, alternatively at least about 45%, alternatively at least about 50%, alternatively at least about 55%, alternatively at least about 60.

In an example, compositions of the disclosure comprise at least one therapeutic dose of mesenchymal lineage precursor or stem cells which, for example, can comprise at least about 100 million cells or about 125 million cells.

Modification of the Cells

The mesenchymal lineage precursor or stem cells of the present disclosure may be altered in such a way that upon administration, lysis of the cell is inhibited. Alteration of an antigen can induce immunological non-responsiveness or tolerance, thereby preventing the induction of the effector phases of an immune response (e.g., cytotoxic T cell generation, antibody production etc.) which are ultimately responsible for rejection of foreign cells in a normal immune response. Antigens that can be altered to achieve this goal include, for example, MHC class I antigens, MHC class II antigens, LFA-3 and ICAM-1.

The mesenchymal lineage precursor or stem cells may also be genetically modified to express proteins of importance for the differentiation and/or maintenance of striated skeletal muscle cells. Exemplary proteins include growth factors (TGF-β, insulin-like growth factor 1 (IGF-1), FGF), myogenic factors (e.g. myoD, myogenin, myogenic factor 5 (Myf5), myogenic regulatory factor (MRF)), transcription factors (e.g. GATA-4), cytokines (e.g. cardiotropin-1), members of the neuregulin family (e.g. neuregulin 1, 2 and 3) and homeobox genes (e.g. Csx, tinman and NKx family).

Compositions of the Disclosure

In one example of the present disclosure the mesenchymal lineage precursor or stem cells and/or progeny thereof and/or soluble factor derived therefrom are administered in the form of a composition. In one example, such a composition comprises a pharmaceutically acceptable carrier and/or excipient. Accordingly, in an example, compositions of the disclosure can comprise culture expanded mesenchymal lineage precursor or stem cells.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for the present disclosure include those conventionally used, e.g., water, saline, aqueous dextrose, lactose, Ringer's solution, a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. For example, such a media composition does not induce any adverse effects in a subject to whom it is administered.

Exemplary carriers and excipients do not adversely affect the viability of a cell and/or the ability of a cell to reduce, prevent or delay metabolic syndrome and/or obesity.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the disclosure may be produced as a liquid for direct application to the blood stream or into a tissue or a region surrounding or adjacent to a tissue, e.g., by injection.

The mesenchymal lineage precursor or stem cells and/or progeny thereof and/or soluble factor derived therefrom can also be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds.

A variety of different scaffolds may be used successfully in the practice of the disclosure. Exemplary scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, (e.g., as described by Vacanti, et al. J. Ped. Surg. 23:3-9 1988; Cima, et al. Biotechnol. Bioeng. 38:145 1991; Vacanti, et al. Plast. Reconstr. Surg. 88:753-9 1991); or synthetic polymers such as polyanhydrides, polyorthoesters, and polylactic acid.

In another example, the mesenchymal lineage precursor or stem cells and/or progeny thereof and/or soluble factor derived therefrom may be administered in a gel scaffold (such as Gelfoam from Upjohn Company).

The compositions described herein may be administered alone or as admixtures with other cells. The cells of different types may be admixed with a composition of the disclosure immediately or shortly prior to administration, or they may be co-cultured together for a period of time prior to administration.

In one example, the composition comprises an effective amount or a therapeutically or prophylactically effective amount of mesenchymal lineage precursor or stem cells and/or progeny thereof and/or soluble factor derived therefrom. For example, the composition comprises about $1\times10^5$ stem cells to about $1\times10^9$ stem cells or about $1.25\times10^3$ stem cells to about $1.25\times10^7$ stem cells/kg (80 kg subject). The exact amount of cells to be administered is dependent upon a variety of factors, including the age, weight, and sex of the subject, and the extent and severity of the disorder being treated.

In an example, $50\times10^6$ to $200\times10^7$ cells are administered. In other examples, $60\times10^6$ to $200\times10^6$ cells or $75\times10^6$ to $150\times10^6$ cells are administered. In an example, $75\times10^6$ cells are administered. In another example, $150\times10^6$ cells are administered.

In an example, the composition comprises greater than $5.00\times10^6$ viable cells/mL. In another example, the composition comprises greater than $5.50\times10^6$ viable cells/mL. In another example, the composition comprises greater than $6.00\times10^6$ viable cells/mL. In another example, the composition comprises greater than $6.50\times10^6$ viable cells/mL. In another example, the composition comprises greater than $6.68\times10^6$ viable cells/mL.

In an example, the methods of the present disclosure encompass administering a total dose of 600 million cells. For example, a subject treated according to the present disclosure can receive multiple doses of an above referenced composition so long as the total dose of cells does not exceed 600 million cells. For example, the subject may receive 3 doses of 200 million cells. In an example, the total dose of cells is 500 million cells. In an example, the total dose of cells is 400 million cells. For example, the subject may receive 4 doses of 100 million cells. In an example, the subject receives 1 dose of 100 million cells at baseline followed by three doses of 100 million cells administered one per month over three months.

In an example, the mesenchymal lineage precursor or stem cells comprise at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% of the cell population of the composition.

Compositions of the disclosure may be cryopreserved. Cryopreservation of mesenchymal lineage precursor or stem cells can be carried out using slow-rate cooling methods or 'fast' freezing protocols known in the art. Preferably, the method of cryopreservation maintains similar phenotypes, cell surface markers and growth rates of cryopreserved cells in comparison with unfrozen cells.

The cryopreserved composition may comprise a cryopreservation solution. The pH of the cryopreservation solution is typically 6.5 to 8, preferably 7.4.

The cryopreservation solution may comprise a sterile, non-pyrogenic isotonic solution such as, for example, PlasmaLyte A™. 100 mL of PlasmaLyte A™ contains 526 mg of sodium chloride, USP (NaCl); 502 mg of sodium gluconate ($C_6H_{11}NaO_7$); 368 mg of sodium acetate trihydrate, USP ($C_2H_3NaO_2 \cdot 3H_2O$); 37 mg of potassium chloride, USP (KCl); and 30 mg of magnesium chloride, USP ($MgCl_2 \cdot 6H_2O$). It contains no antimicrobial agents. The pH is adjusted with sodium hydroxide. The pH is 7.4 (6.5 to 8.0).

The cryopreservation solution may comprise Profreeze™. The cryopreservation solution may additionally or alternatively comprise culture medium, for example, αMEM.

To facilitate freezing, a cryoprotectant such as, for example, dimethylsulfoxide (DMSO), is usually added to the cryopreservation solution. Ideally, the cryoprotectant should be nontoxic for cells and patients, nonantigenic, chemically inert, provide high survival rate after thawing and allow transplantation without washing. However, the most commonly used cryoprotector, DMSO, shows some cytotoxicity. Hydroxyethyl starch (HES) may be used as a substitute or in combination with DMSO to reduce cytotoxicity of the cryopreservation solution.

The cryopreservation solution may comprise one or more of DMSO, hydroxyethyl starch, human serum components and other protein bulking agents. In one example, the cryopreserved solution comprises about 5% human serum albumin (HSA) and about 10% DMSO. The cryopreservation solution may further comprise one or more of methylcellulose, polyvinyl pyrrolidone (PVP) and trehalose.

In one embodiment, cells are suspended in 42.5% Profreeze™/50% αMEM/7.5% DMSO and cooled in a controlled-rate freezer.

The cryopreserved composition may be thawed and administered directly to the subject or added to another solution, for example, comprising HA. Alternatively, the cryopreserved composition may be thawed and the mesenchymal lineage precursor or stem cells resuspended in an alternate carrier prior to administration.

In an example, cellular compositions of the disclosure can comprise Plasma-Lyte A, dimethyl sulfoxide (DMSO) and human serum albumin (HSA). For example, compositions of the disclosure may comprise Plasma-Lyte A (70%), DMSO (10%), HSA (25%) solution, the HSA solution comprising 5% HSA and 15% buffer.

In an example, the compositions described herein may be administered as a single dose.

In some examples, the compositions described herein may be administered over multiple doses. For example, at least 2, at least 3, at least 4 doses. In other examples, compositions described herein may be administered over at least 5, at least 6, at least 7, at least 8, at least 9, at least 10 doses.

In one example, the mesenchymal lineage precursor or stem cells can be culture expanded prior to administration to a subject. Various methods of cell culture are known in the art. In an example, mesenchymal lineage precursor or stem cells are culture expanded for about 4-10 passages. In an example, mesenchymal lineage precursor or stem cells are culture expanded for at least 4, at least 5, at least 6, at least 7, at least 8, at least 9, at least 10 passages. In an example, mesenchymal lineage precursor or stem cells are culture expanded for at least 5 passages. In these examples, stem cells may be culture expanded before being cryopreserved.

In an example, mesenchymal lineage precursor or stem cells are culture expanded in a serum free medium prior to administration.

In some examples, the cells are contained within a chamber that does not permit the cells to exit into a subject's circulation but permits factors secreted by the cells to enter the circulation. In this manner soluble factors may be administered to a subject by permitting the cells to secrete the factors into the subject's circulation. Such a chamber may equally be implanted at a site in a subject to increase local levels of the soluble factors.

In an example, mesenchymal lineage precursor or stem cells may be administered systemically. In an example, mesenchymal lineage precursor or stem cells may be administered to the subjects airway. In an example, mesenchymal lineage precursor or stem cells may be administered to the lung(s) of a subject. In another example, compositions of the disclosure are administered intravenously. In another example, compositions are administered intravenously and to the subjects airway.

In an example, mesenchymal lineage precursor or stem cells are administered once weekly. For example, mesenchymal lineage precursor or stem cells can be administered once weekly every two weeks. In an example, mesenchymal lineage precursor or stem cells can be administered once monthly. In an example, two doses of mesenchymal lineage precursor or stem cells are administered once weekly over two weeks. In another example, two doses of mesenchymal lineage precursor or stem cells are administered once weekly every two weeks. In another example, four doses of mesenchymal lineage precursor or stem cells are administered over two weeks before subsequent doses are administered monthly. In an example, two doses of mesenchymal lineage precursor or stem cells can be administered once weekly every two weeks before subsequent doses are administered once monthly. In an example, four doses are administered monthly.

In an example, a composition comprising cells is administered according to the present disclosure to subjects with elevated circulating CRP levels. In an example, the methods of the present disclosure comprise the steps of: i) selecting a subject with an inflammatory lung disease who has a circulating CRP level of greater than or equal to 2 mg/L, and ii) administering to the subject a composition comprising mesenchymal lineage precursor or stem cells (MLPSCs). In an example, the subjects circulating CRP level is greater than or equal to 3 mg/L. In another example, the subjects circulating CRP level is greater than or equal to 4 mg/L. In an example, mesenchymal stem cells are administered to the subject. In another example, the subject has one or both of COPD and ARDS according to the present disclosure. In an example, selecting involves obtaining one or more samples from the subject to be treated and measuring the circulating CRP level in the sample(s).

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The following specific examples are to be construed as merely illustrative, and not limitative of the remainder of the disclosure in any way whatsoever. Without further elaboration, it is believed that one skilled in the art can, based on the description herein, utilize the present invention to its fullest extent.

The present application claims priority from Australian Provisional Patent Application 2020900685 filed 5 Mar. 2020, the entire contents of which are incorporated herein by reference.

EXAMPLES

Ex-vivo Culture-Expanded Adult Allogeneic Bone Marrow Derived Mesenchymal Stem Cells (MSCs), for the Treatment of Inflammatory Lung Disease

Composition

The composition is comprised of culture-expanded mesenchymal stromal cells (ceMSC) isolated from the bone marrow of healthy adult donors. The final composition comprises ceMSC formulated in Plasma-Lyte A, dimethyl sulfoxide (DMSO) and human serum albumin (HSA).

Objectives

To determine:
Safety
Fev1 Change from Baseline.
Change from Baseline in FEV1/FVC.
FVC Change from Baseline.
Change from Baseline total 6 MW distance.

Measurements

Spirometry measurements including FEV1, and FVC, were taken after administration of a bronchodilator. Baseline measurements were considered to be those taken post bronchodilator, prior to the first study drug infusion at Visit 2 (Study Day 0). Administration of spirometry tests was conducted in accordance with the American Association for Respiratory Care (AARC) Spirometry Clinical Practice Guideline (www.rcjournal.com/cpgs/spirupdatecpg.html).

A 6 minute walk test (MWT) was performed at all study visits. The procedure for the 6 MWT followed the American Thoracic Society guidelines. Heart rate and SaO2 were recorded before and after walking. Distance walked in 6 minutes along a 30-meter (100 foot) hallway was also recorded along with the subject's level of dyspnea and level of fatigue using the Borg scale before and after walking.

Subjects

Chronic Obstructive Pulmonary Disease (COPD) patients were stratified into the following three groups based on circulating CRP levels at baseline (i.e. before treatment):
those with circulating CRP levels ≥4 mg/ml and those with circulating CRP levels <4 mg/ml at baseline;
those with circulating CRP levels ≥3 mg/ml and those with circulating CRP levels <3 mg/ml at baseline;
those with circulating CRP levels ≥2 mg/ml and those with circulating CRP levels <2 mg/ml at baseline.
All COPD patients had their inflammatory lung disease treated with monthly doses of MSCs delivered intravenously. Subjects received 100 million MSCs at baseline (day 0) and then three further doses of 100 million cells administered once per month (days 30, 60 and 90). FEV1, FVC and 6 min walk test were analyzed at day 120 (30 days after their final dose was administered).

Analysis

The patient group with a circulating CRP of ≥4 mg/L showed significantly improved lung function following treatment with the cells compared with those treated with a placebo (FIGS. 1 to 4; Tables 1 and 4). For example, within 120 days from the first dose the patient group with CRP of ≥4 mg/L receiving MSCs had an FEV1 change from baseline of 0.0625 compared to −0.1 in the placebo group (FIG. 1). Within 150 days from the first dose the patient group with CRP of ≥4 mg/L receiving MSCs had an FEV1/FVC change from baseline of 0.02 compared to 0.002 in the placebo group (FIG. 2). Within 120 days from the first dose the patient group with CRP of ≥4 mg/L receiving MSCs had an FVC change from baseline of 0.11 compared to −0.25 in the placebo group (FIG. 3). Within 120 days from the first dose the patient group with CRP of ≥4 mg/L receiving MSCs demonstrated an improvement in the Six-minute walk test of 52.2 meters compared to about −3.1 meters in the placebo group (FIG. 4).

The patient group with a circulating CRP of ≥3 mg/L also showed significantly improved lung function following treatment with the cells compared with those treated with a placebo (Table 2). For example, within 120 days from the first dose the patient group with CRP of ≥3 mg/L receiving MSCs had an FEV1 change from baseline of 0.05 compared to −0.1 in the placebo group. Within 120 days from the first dose the patient group with CRP of ≥3 mg/L receiving MSCs had an FVC change from baseline of 0.11 compared to −0.22 in the placebo group. Within 120 days from the first dose the patient group with CRP of ≥4 mg/L receiving MSCs demonstrated an improvement in the Six-minute walk test of 42.6 meters compared to about 6.0 meters in the placebo group.

The patient group with a circulating CRP of ≥2 mg/L also showed significantly improved lung function following treatment with the cells compared with those treated with a placebo (Table 3). For example, within 120 days from the first dose the patient group with CRP of ≥2 mg/L receiving MSCs had an FVC change from baseline of 0.042 compared to −0.20 in the placebo group.

These results show a surprising effect in that the MSC treatment showed progressively greater benefit in patients who have progressively increased levels of circulating CRP. As such patients with circulating CRP of 2 mg/ml responded less well than patients with circulating CRP of 3 mg/ml who respond less well than patients with circulating CRP of 4 mg/ml. This is unexpected given that efficacy of small molecule therapy or other biologics (e.g. monoclonal antibodies) have greatest efficacy in patients with lowest levels of inflammation as measured by circulating CRP and their effects progressively wane as levels of CRP increase.

TABLE 1

Day 120 Efficacy Analysis for CRP Subgroups: Subjects with Baseline CRP ≥4 mg/ml compared with subjects with Baseline CRP <4 mg/ml.

| Subgroup/Parameter | Placebo | MSC | Difference | P-value** |
|---|---|---|---|---|
| Baseline CRP ≥4 Mean Change from Baseline: | N = 17 | N = 12 | | |
| FEV1 (L) | −0.0935 | 0.0625 | 0.1560 | 0.0027 |
| FVC (L) | −0.2494 | 0.1108 | 0.3602 | 0.0092 |

TABLE 1-continued

Day 120 Efficacy Analysis for CRP Subgroups: Subjects with Baseline
CRP ≥4 mg/ml compared with subjects with Baseline CRP <4 mg/ml.

|  | Placebo | MSC | Difference | P-value** |
|---|---|---|---|---|
| 6-Minute Walk Distance (meters) | −3.1176 | 52.1667 | 55.2843 | 0.0041 |
| Baseline CRP <4 | N = 15 | N = 18 | | |
| Mean Change from Baseline: | | | | |
| FEV1 (L) | −0.00867 | −0.0828 | −0.0741 | 0.1229 |
| FVC (L) | −0.0507 | −0.1217 | −0.0710 | 0.4606 |
| 6-Minute Walk Distance (meters) | 38.9333 | 10.3333 | −28.6000 | 0.1163 |

**p-value from Student's t-test.

TABLE 2

Day 120 Efficacy Analysis for CRP Subgroups: Subjects with Baseline
CRP ≥3 mg/ml compared with subjects with Baseline CRP <3 mg/ml.

|  | Placebo | MSC | Difference | P-value** |
|---|---|---|---|---|
| Subgroup/Parameter | | | | |
| Baseline CRP ≥3 | N = 21 | N = 14 | | |
| Mean Change from Baseline: | | | | |
| FEV1 (L) | −0.0743 | 0.0507 | 0.1250 | 0.0085 |
| FVC (L) | −0.2167 | 0.1093 | 0.3260 | 0.0062 |
| 6-Minute Walk Distance (meters) | 5.9524 | 42.5714 | 36.6190 | 0.0404 |
| Baseline CRP <3 | N = 11 | N = 16 | | |
| Mean Change from Baseline: | | | | |
| FEV1 (L) | −0.0145 | −0.0906 | −0.0761 | 0.1645 |
| FVC (L) | −0.0409 | −0.1494 | −0.1085 | 0.3325 |
| 6-Minute Walk Distance (meters) | 36.9091 | 13.5000 | −23.4091 | 0.2701 |

**p-value from Student's t-test.

TABLE 3

Day 120 Efficacy Analysis for CRP Subgroups: Subjects with Baseline
CRP ≥2 mg/ml compared with subjects with Baseline CRP <3 mg/ml.

|  | Placebo | MSC | Difference | P-value ** |
|---|---|---|---|---|
| Subgroup/Parameter | | | | |
| Baseline CRP ≥2 | N = 23 | N = 19 | | |
| Mean Change from Baseline: | | | | |
| FEV1 (L) | −0.0730 | 0.00947 | 0.0825 | 0.0553 |
| FVC (L) | −0.1991 | 0.0416 | 0.2407 | 0.0218 |
| 6-Minute Walk Distance (meters) | 8.3913 | 31.6316 | 23.2403 | 0.1594 |
| Baseline CRP <2 | N = 9 | N = 11 | | |
| Mean Change from Baseline: | | | | |
| FEV1 (L) | −0.00444 | −0.0836 | −0.0792 | 0.2345 |
| FVC (L) | −0.0467 | −0.1500 | −0.1033 | 0.4345 |
| 6-Minute Walk Distance (meters) | 37.5556 | 19.1818 | −18.3737 | 0.4444 |

**p-value from Student's t-test.

TABLE 4

Statistical Analysis of Fev1 (L) and 6-minute walk distance (meters),
Change from Baseline Subjects with Baseline CRP ≥4 mg/ml.

| | Number of Subjects Placebo/ Active | FEV1 Change from Baseline (L) | Change from Baseline in 6-minute walk distance (meters) |
|---|---|---|---|
| Overall treatment effect p-value* | 29 (17/12) | 0.0147 | 0.0063 |

| Study Visit | Study day | Number of Subjects | Treatment difference p-value** | Treatment difference p-value** |
|---|---|---|---|---|
| 4 | 30 | 29 (17/12) | 0.1201 | 0.2176 |
| 5 | 60 | 29 (17/12) | 0.0801 | 0.0118 |
| 6 | 90 | 29 (17/12) | 0.0511 | 0.0967 |
| 7 | 120 | 29 (17/12) | 0.0027 | 0.0041 |
| 8 | 150 | 27 (16/11) | 0.1786 | 0.0938 |
| 9 | 180 | 27 (16/11) | 0.2571 | 0.3463 |
| 10 | 360 | 24 (14/10) | 0.3404 | 0.4338 |
| 11 | 720 | 24 (14/10) | 0.1258 | 0.2896 |

*Overall treatment effect across all visits using mixed-effect model with repeated measures (MMRM).
**Simple Differences of treatment by visit Least Squares Means, using mixed-effect model with repeated measures (MMRM).

The invention claimed is:

1. A method of treating an inflammatory lung disease in a human subject in need thereof, the method comprising administering to the subject a composition comprising a population of culture expanded mesenchymal lineage precursor or stem cells (MLPSCs), wherein the subject has a circulating C-reactive protein (CRP) level of ≥2 mg/L, wherein the inflammatory lung disease is selected from the group consisting of Chronic Obstructive Pulmonary Disease (COPD), Pulmonary Arterial Hypertension (PAH), and asthma, and wherein the subject has an improvement in one or more of the following after treatment:

Forced expiratory volume in one second (FEV1);
Forced vital capacity (FVC);
FEV1/FVC and;
6 minute walk test.

2. The method of claim 1, wherein the MLPSCs are culture expanded from an intermediate cryopreserved MLP-SCs population.

3. The method of claim 1, wherein the composition is administered intravenously.

4. The method of claim 1, wherein the MLPSCs are mesenchymal stem cells (MSCs).

5. The method of claim 1, which comprises administering between $1\times10^7$ and $2\times10^8$ cells per dose, wherein a dose is administered at baseline followed by 3 subsequent monthly doses over 90 days.

6. The method of claim 1, which comprises administering about $1\times10^8$ cells per dose, wherein a dose is administered at baseline followed by 3 subsequent monthly doses over 90 days.

7. The method of claim 1, wherein the subject has an FEV1 change from baseline of at least 0.02, within 120 days of treatment.

8. The method of claim 1, wherein the subject has an FEV1 change from baseline of at least 0.05, within 120 days of treatment.

9. The method of claim 1, wherein the subject has an FVC change from baseline of at least 0.05, within 120 days of treatment.

10. The method of claim 1, wherein the subject has an FVC change from baseline of at least 0.1, within 120 days of treatment.

11. The method of claim 1, wherein the subject has an FEV1/FVC change from baseline of at least 0.01, within 120 days of treatment.

12. The method of claim 1, wherein the subject has an FEV1/FVC change from baseline of at least 0.015, within 120 days of treatment.

13. The method of claim 1, wherein the subject shows an improvement in the 6 minute walk test of at least 40 meters, within 60 days or within 120 days of treatment.

14. The method of claim 1, wherein the subject shows an improvement in the 6 minute walk test of at least 50 meters, within 60 days or within 120 days of treatment.

15. The method of claim 1, wherein the composition comprises greater than $6.68\times10^6$ viable cells/mL.

* * * * *